United States Patent
Patterson et al.

(10) Patent No.: US 6,479,548 B2
(45) Date of Patent: Nov. 12, 2002

(54) SUBSTITUTED STILBENES AS GLUCOSE UPTAKE ENHANCERS

(75) Inventors: John Patterson, Mountain View, CA (US); Sophia Park, Emeryville, CA (US); Robert T. Lum, Palo Alto, CA (US); Wayne R. Spevak, Albany, CA (US)

(73) Assignee: Telik, Inc., South San Francisco, CA (US)

( * ) Notice: Subject to any disclaimer, the term of this patent is extended or adjusted under 35 U.S.C. 154(b) by 0 days.

(21) Appl. No.: 09/872,763

(22) Filed: May 31, 2001

(65) Prior Publication Data

US 2002/0032218 A1 Mar. 14, 2002

Related U.S. Application Data

(60) Provisional application No. 60/208,591, filed on Jun. 2, 2000.

(51) Int. Cl.[7] ............... A61K 31/195; A61K 31/24; C07C 229/00
(52) U.S. Cl. ............... 514/567; 514/534; 514/538; 514/562; 514/564; 560/19; 562/457
(58) Field of Search ............... 562/48, 51, 457; 514/866, 562, 567, 564, 534, 538; 560/19

(56) References Cited

U.S. PATENT DOCUMENTS 5,681,832 A * 10/1997 Haugwitz et al.
5,830,918 A * 11/1998 Sportsman et al.
6,326,510 B1   12/2001 Bernardon ............... 560/56

FOREIGN PATENT DOCUMENTS

FR   2 759 368    8/1998
JP   268169/1997  10/1997

OTHER PUBLICATIONS

Lewis et al, Luminescence of N–Arylbenzamides in Low-Temperature Glasses, Journal of Physical Chemistry A 1999, 103, pp. 9678–9686.*

Chemical Abstracts, 68(20), 91457x (1968), and Izmail'skii et al., "The origin of the spectra of 4–benzoylaminostilbene derivatives based on quasi–atomic chromophore systems", Dokl. Akad. Nauk. SSSR, 177(5), 1091–1094 (1967).

* cited by examiner

Primary Examiner—Samuel Barts
Assistant Examiner—Paul A. Zucker
(74) Attorney, Agent, or Firm—Heller Ehrman White & McAuliffe LLP

(57) ABSTRACT

Compound of formula I

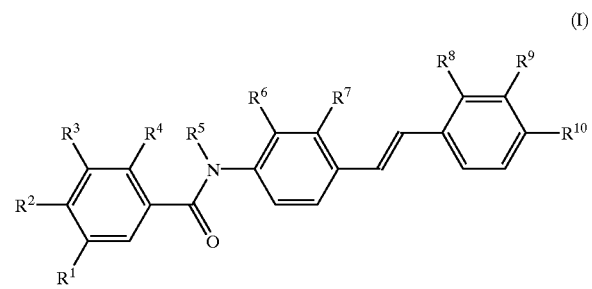

activate the insulin receptor kinase. Pharmaceutical compositions comprising the compounds, and methods of treatment of hyperglycemia and other diseases involving imbalance of glucose levels, especially for the treatment of type II diabetes, by administering these compounds to mammalian hosts, and processes for their preparation, are also described.

22 Claims, No Drawings

SUBSTITUTED STILBENES AS GLUCOSE UPTAKE ENHANCERS

This application claims the priority under 35 USC 119(e) of Provisional Application No. 60/208,591, filed Jun. 2, 2000, and incorporated by reference herein.

BACKGROUND OF THE INVENTION (a) Field of The Invention

The present invention relates to chemical compounds that activate the insulin receptor kinase, and to methods for treating humans with hyperglycemia, especially for the treatment of Type II diabetes.

(b) Description of Related Art

Peptide and protein hormones, such as insulin, interact with receptors with high specificity. The insulin receptor is present on virtually all cells and at high concentrations on the cells for the liver, skeletal muscles, and adipose tissue. Stimulation of the insulin receptor with insulin is an essential element in carbohydrate metabolism and storage.

Diabetics either lack sufficient endogenous secretion of the insulin hormone (Type I diabetes) or have an insulin receptor-mediated signaling pathway that is resistant to endogenous or exogenous insulin (Type II diabetes, or non-insulin-dependent diabetes mellitus (NIDDM)). Type II diabetes is the most common form of diabetes, affecting about 5% of individuals in the industrialized nations. In Type II diabetics, major insulin-responsive tissues such as liver, skeletal muscle, and fat exhibit insulin resistance [Haring and Mehnert, *Diabetologia* 36:176–182 (1993); Haring et al., *Diabetologia*, 37 Suppl. 2:S149–54 (1994)]. The resistance to insulin in Type II diabetes is complex and likely multi-factorial but appears to be caused by an impaired signal from the insulin receptor to the glucose transport system and to glycogen synthase. Impairment of the insulin receptor kinase has been implicated in the pathogenesis of this signaling defect. Insulin resistance is also found in many non-diabetic individuals and may be an underlying etiologic factor in the development of the disease [Reaven, *Diabetes*, 37:1595–1607 (1988)].

Considerable information is known concerning the insulin receptor itself. The receptor consists of four separate subunits consisting of two identical α and two identical β chains. The β subunits contain tyrosine kinase activity and the ATP binding sites. The insulin receptor is activated by autophosphorylation of key tyrosine residues in its cytoplasmic tyrosine kinase domain. This autophosphorylation is required for subsequent activity of the insulin receptor. The autophosphorylation stabilizes the activated receptor kinase, resulting in a phosphorylation cascade involving intracellular signaling proteins.

At present, there are limited pharmacological approaches to treatment of Type II diabetes. Insulin is currently used as a treatment but is disadvantageous, because insulin must be injected. Although several peptide analogs of insulin have been described, none with a molecular weight below 5000 Dalton retains activity. Some peptides which interact with sites on the β-subunit of the insulin receptor have shown enhancement of the activity of insulin on its receptor [Kole et al., *J. Biol. Chem.* 271:31619–31626 (1996); Kasuya et al., *Biochem. Biophys. Res. Commun.*, 200:777–783 (1994)]. Kohanski and others have reported on a variety of polycationic species that generate a basal effect but do little to enhance insulin action [Kohanski, *J. Biol. Chem.* 264:20984–20991 (1989); Xu et al., *Biochemistry* 30:11811–11819 (1991)]. These peptides apparently act on the cytoplasmic kinase domain of the insulin receptor.

In addition, certain non-peptide components have been found to enhance the effects of insulin, but none appear to act directly on the insulin receptor kinase. For example, thiazolidinediones, such as pioglitazone, enhance adipocyte differentiation [Kletzien et al., *Mol. Pharmacol.* 41:393 (1992). These thiazolidinediones represent a class of potential anti-diabetic compounds that enhance the response of target tissues to insulin [Kobayashi, *Diabetes*, 41:476 (1992)]. The thiazolidinediones switch on peroxisome proliferator-activated receptor γ (PPARγ), the nuclear transcription factor involved in adipocyte differentiation [Kliewer et al., *J. Biol. Chem.*, 270:12953 (1995)], and do not have a direct effect on the insulin receptor kinase. Other anti-diabetic agents currently in use include both insulin secretagogues (such as the sulfonylureas) and biguanides (such as methformin) that inhibit hepatic glucose output.

Stilbenes and derivatives are prevalent throughout the chemical literature, with a large number of functionalized stilbenes described. Tri- and tetra- aryl stilbenes are known but have relatively few examples. The substituted stilbenes have biological activity and are reported as treatments to inflammatory and proliferative skin diseases [Nusbaumer, PCT International Publication No. WO 96/28430], as a method for inhibiting apoptosis [Babior et al., PCT International Publication No. WO 9634604], and as anti-virals [Haugwitz et al., PCT International Publication No. WO 9625399]. Tetra-substituted stilbenes, such as tamoxifen, are used in treating breast cancer [Furr et al., *Pharmacol. Ther.* 25:127–205 (1984)]. There is extensive literature describing the use of the stilbenes in the preparation of interesting polymers.

The disclosures of these and other documents referred to elsewhere in this application are incorporated herein by reference.

SUMMARY OF THE INVENTION

In a first aspect, the invention is compounds of formula I:

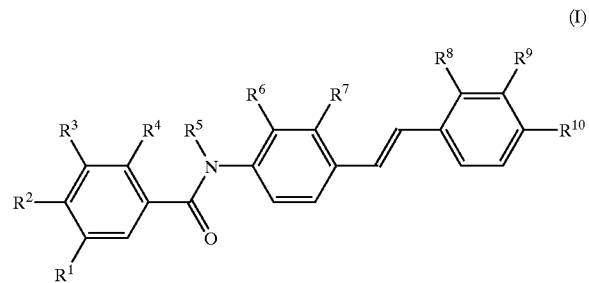

(I)

where

R$^1$, R$^3$, and R$^4$ are, independently, hydrogen, lower alkyl, substituted lower alkyl, halo, hydroxyl, optionally substituted lower alkyloxy, —NR$^{11}$R$^{12}$, or —C(O)NR$^{11}$R$^{12}$, where R$^{11}$ and R$^{12}$ are, independently, hydrogen, lower alkyl, substituted lower alkyl, aryl, substituted aryl, aryl(lower)alkyl, substituted aryl(lower)alkyl, heteroaryl(lower)alkyl, substituted heteroaryl(lower)alkyl, heterocyclyl, substituted heterocyclyl, heteroaryl, or substituted heteroaryl, or —C(O)OR$^{13}$ where R$^{13}$ is hydrogen or lower alkyl;

R$^2$ is hydrogen, lower alkyl, substituted lower alkyl, halo, hydroxyl, lower alkoxy, substituted lower alkyloxy, carboxyl, —NR$^{11}$R$^{12}$, —NR$^{11}$C(O)R$^{12}$, or —C(O)NR$^{11}$R$^{12}$, where R$^{11}$ and R$^{12}$ have the above meanings, or $R^2$ and $R^3$, together with the carbon atoms to which they are attached, form a heterocyclic ring;

$R^5$ is hydrogen, lower alkyl, substituted lower alkyl, or aryl;

$R^6$ and $R^7$ are, independently, hydrogen, lower alkyl or —C(O)OR$^{13}$, where $R^{13}$ has the above meaning;

$R^8$ and $R^9$ are, independently, hydrogen, lower alkyl, substituted lower alkyl, halo, hydroxyl, lower alkoxy, carboxyl, —NR$^{11}$R$^{12}$, or —C(O)N R$^{11}$R$^{12}$, where $R^{11}$ and $R^{12}$ have the above meanings, $R^{10}$ is hydrogen, lower alkyl, substituted lower alkyl, halo, hydroxy, lower alkoxy, —C(O)OR$^{13}$ where $R^{13}$ is hydrogen or lower alkyl, —SO$_3$H, or —C(O)NR$^{11}$R$^{12}$, where $R^{11}$ and $R^{12}$ have the above meanings;

and the pharmaceutically acceptable salts thereof; as single stereoisomers or mixtures of stereoisomers.

These compounds are useful for stimulating and/or enhancing the uptake of glucose into cells in a mammal or for treating a mammalian disease state selected from the group consisting of hyperglycemia, type I diabetes, and type II diabetes.

In a second embodiment, this invention is pharmaceutical compositions comprising (a) at least one pharmaceutically acceptable carrier and (b) a compound of the first aspect of the invention as the active ingredient.

These compositions are useful for stimulating and/or enhancing the uptake of glucose into cells in a mammal or for treating a mammalian disease state selected from the group consisting of hyperglycemia, type I diabetes, and type II diabetes.

In a third embodiment, this invention is methods of treatment of hyperglycemia, type I diabetes, or type II diabetes in a mammal, such as a human, by administering a therapeutically effective amount of a compound of the first aspect of the invention, or a composition of the second aspect of the invention.

In a fourth embodiment, this invention is a method of stimulating the kinase activity of the insulin receptor or activating the insulin receptor, comprising contacting the insulin receptor or the kinase portion thereof with a compound of the first aspect of the invention in an amount sufficient to stimulate the kinase activity of the insulin receptor or activate the insulin receptor.

In a fifth embodiment, this invention provides a method for stimulating the uptake of glucose into cells which display the insulin receptor, comprising contacting the cells, in the presence of insulin, with a compound of the first aspect of the invention in an amount sufficient to stimulate the uptake of glucose into the cells. The uptake of glucose into cells in a mammal may be effected by administering the compound, or a composition containing it, to the mammal.

In a sixth embodiment, this invention provides processes for the preparation of compounds of formula I or pharmaceutically acceptable salts thereof.

Certain compounds of formula I are useful as intermediates to prepare other compounds of formula I with higher activity.

DETAILED DESCRIPTION OF THE INVENTION

Definitions and General Parameters

"Alkyl" means a linear $C_{1-20}$ monovalent hydrocarbyl group or a branched or cyclic $C_{3-20}$ monovalent hydrocarbyl group.

"Lower alkyl", as in "lower alkyl", "halo-lower alkyl", "aryl(lower)alkyl", or "heteroaryl(lower)alkyl", means a $C_{1-10}$ alkyl. The term "lower alkyl" includes such groups as methyl, ethyl, isopropyl, propyl, butyl, isobutyl, sec-butyl, tert-butyl, pentyl, hexyl, n-decyl, cyclopropyl, cyclopentyl, cyclopropylmethyl, cyclohexyl, or cyclohexylmethyl. $C_{1-6}$ lower alkyls are preferred. "Lower alkyloxy" is a group of the formula —O—R$^a$ where R$^a$ is a "lower alkyl" as defined above.

"Substituted alkyl" or "substituted lower alkyl" indicates that the alkyl group or the lower alkyl group is typically mono-, di-, or tri-substituted with a moiety such as aryl, R'-substituted aryl, heteroaryl, nitro, cyano, halo, —OR, —SR, —C(O)R, —OC(O)R, —C(O)OR, —NR$_2$, —OSO$_2$R, —SO$_2$OR, —SO$_2$NR$_2$, —NRSO$_2$R, —C(O)NR$_2$, or —NRC(O)R, where each R is, independently, hydrogen, lower alkyl, R'-substituted lower alkyl, aryl, R'-substituted aryl, heteroaryl, heteroaryl(lower)alkyl, R'-substituted aryl(lower) alkyl, or aryl(lower)alkyl and each R' is, independently, hydroxy, halo, lower alkyloxy, cyano, thio, nitro, lower alkyl, halo-lower alkyl, amino, or —C(O)OR$^b$ where R$^b$ is hydrogen or alkyl. Substituted alkyls or substituted lower alkyls which are substituted with one to three of the substituents selected from the group consisting of cyano, halo, lower alkyloxy, thio, nitro, amino, or hydroxy are particularly preferred.

"Substituted alkyloxy" or "substituted lower alkyloxy" is a group of the formula —O—R$^c$ where R$^c$ is "substituted alkyl" or "substituted lower alkyl" as defined above.

"Halo-lower alkyl" means a lower alkyl substituted with one to three halo groups, and is further exemplified by such groups as —CF$_3$, —CH$_2$CF$_3$ and —CH$_2$CCl$_3$.

"Aryl", as in "aryl", "aryloxy", and "aryl(lower)alkyl", means a group derived from an aromatic hydrocarbon containing 6 to 20 ring carbon atoms, having a single ring (e.g., phenyl), two or more condensed rings, preferably 2 to 3 condensed rings (e.g., naphthyl), or two or more aromatic rings, preferably 2 or 3 aromatic rings, which are linked by a single bond (e.g., biphenyl). The aryl is preferably $C_6$–$C_{16}$ and even more preferably, $C_6$–$C_{14}$.

A "substituted aryl" is an aryl group which is typically mono-, di-, or tri-substituted, independently, with a moiety such as lower alkyl, R$^d$-substituted lower alkyl, nitro, cyano, halo, —OR$^e$, —SR$^e$, —C(O)R$^e$, —C(O)OR$^e$, —OC(O)R$^e$, —NR$^e{}_2$, —OSO$_2$R$^e$, —SO$_2$OR$^e$, —SO$_2$NR$^e{}_2$, —NRSO$_2$R$^e$, —C(O)NR$^e{}_2$, or —NRC(O)R$^e$, where each R$^d$ is, independently, hydroxy, halo, lower alkyloxy, cyano, thio, nitro, lower alkyl, halo-lower alkyl, or amino, and each R$^e$ is, independently, hydrogen, lower alkyl, R$^d$-substituted lower alkyl, aryl, R$^d$-substituted aryl, heteroaryl, heteroaryl(lower) alkyl, R$^d$-substituted aryl(lower) alkyl, or aryl(lower)alkyl. Especially preferred substituents on a substituted aryl are lower alkyl, halo-lower alkyl, halo, cyano, thio, nitro, amino, lower alkyloxy, hydroxy, —SO$_2$OR$^f$, —SO$_2$NR$^f{}_2$, —C(O)OR$^f$, and —C(O)NR$^f{}_2$, where R$^f$ is a hydrogen or lower alkyl.

"Heteroaryl", as in "heteroaryl" and "hetero(lower)alkyl", means a group derived from an aromatic hydrocarbon containing 5 to 14 ring atoms, 1 to 5 of which are hetero atoms chosen, independently, from N, O, or S, and includes monocyclic, condensed heterocyclic, and condensed carbocyclic and heterocyclic aromatic rings (e.g. thienyl, furyl, pyrrolyl, pyrimidinyl, isoxazolyl, oxazolyl, indolyl, isobenzofuranyl, purinyl, isoquinolyl, pteridinyl, imidazolyl, pyridyl, pyrazolyl, pyrazinyl, quinolyl, etc.).

A "substituted heteroaryl" may have from one to three substituents such as lower alkyl, R$^d$-substituted lower alkyl, nitro, cyano, halo, —OR$^g$, —SR$^g$, —C(O)R$^g$, —C(O)OR$^g$, —OC(O)R$^g$, —NR$^g_2$, —OSO$_2$R$^g$, —SO$_2$OR$^g$, —SO$_2$NR$^g_2$, —NRSO$_2$R$^g$, —C(O)NR$^g_2$, or —NRC(O)R$^g$, where each R$^g$ is, independently, hydrogen, lower alkyl, R$^d$-substituted lower alkyl, aryl, R$^d$-substituted aryl, heteroaryl, heteroaryl (lower)alkyl, R$^d$-substituted aryl(lower) alkyl, or aryl(lower) alkyl and each R$^d$ is as defined above. In addition, any two adjacent substituents on the heteroaryl may optionally together form a lower alkylenedioxy. Particularly preferred substituents on the heteroaryl include hydroxy, halo, lower alkyloxy, cyano, thio, nitro, lower alkyl, halo-lower alkyl, or ammo.

"Heterocyclyl" or "heterocyclic ring" means a saturated cyclic (mono- or bicyclic) group containing 5 to 14 ring atoms and having at least one ring atom other than carbon. Preferably, 1 to 5 of the hetero atoms are chosen, independently, from N, O, or S. Monocyclic heterocyclyls are, for example, tetrahydrofuranyl, tetrapyranyl, piperidinyl, etc.

A "substituted heterocyclyl" may have from one to three substituents such as lower alkyl, R$^d$-substituted lower alkyl, nitro, cyano, halo, —OR$^g$, —SR$^g$, —C(O)R$^g$, —C(O)OR$^g$, —OC(O)R$^g$, —NR$^g_2$, —OSO$_2$R$^g$, —SO$_2$OR$^g$, —SO$_2$NR$^g_2$, —NRSO$_2$R$^g$, —C(O)NR$^g_2$, or —NRC(O)R$^g$, where each R$^g$ is, independently, hydrogen, lower alkyl, R$^d$-substituted lower alkyl, aryl, R$^d$-substituted aryl, heteroaryl, heteroaryl (lower)alkyl, R$^d$-substituted aryl(lower) alkyl, or aryl(lower) alkyl and each R$^d$ is as defined above. Preferred substituents on a substituted heterocyclyl include lower alkyl, halo-lower alkyl, cyano, thio, amino, lower alkyloxy, or hydroxy.

"Aryl(lower)alkyl" means a lower alkyl group which is substituted with an aryl group, as previously defined. A "substituted aryl(lower)alkyl" means an aryl(lower)alkyl group having one to three substituents on the aryl portion or the alkyl portion of the group, or both.

"Heteroaryl(lower)alkyl" means a lower alkyl group which is substituted with a heteroaryl group, as previously defined. A "substituted heteroaryl(lower)alkyl" means a heteroaryl(lower)-alkyl group having one to three substituents on the heteroaryl portion or the alkyl portion of the group, or both.

"Halo" means bromo, iodo, fluoro, or chloro.

A "pharmaceutically acceptable salt" may be any salt derived from an inorganic or organic acid or an inorganic or organic base. The term "pharmaceutically acceptable anion" refers to the anion of such acid addition salts. The term "pharmaceutically acceptable cation" refers to a cation formed by addition of base.

"Inner salts" or "zwitterions" can be formed by transferring a proton from a carboxyl group onto the lone pair of electrons of the nitrogen atom in an amino group if both such groups are present in the compound.

A "therapeutically effective amount" means the amount which, when administered to a mammal for treating a disease, is sufficient to effect such treatment for the disease.

"Treating" or "treatment" of a disease in a mammal includes:
(1) preventing the disease from occurring in a mammal which may be predisposed to the disease but does not yet experience or display symptoms of the disease;
(2) inhibiting the disease, i.e., arresting its development, or
(3) relieving the disease, i.e., causing regression of the disease.

"Disease" here includes hyperglycemia and diabetes (both Type I and Type A).

The "kinase portion thereof", with respect to the insulin receptor, means the cytoplasmic tyrosine kinase domain of the insulin receptor.

"Stereoisomers" means compounds that have the same sequence of covalent bonds and differ in the relative disposition of their atoms in space.

Compounds and Pharmaceutical Compositions

In a first aspect, the invention is compounds of formula I:

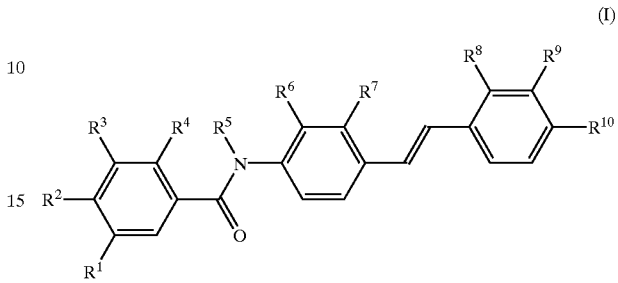

where
R$^1$, R$^3$, and R$^4$ are, independently, hydrogen, lower alkyl, substituted lower alkyl, halo, hydroxyl, optionally substituted lower alkyloxy, —NR$^{11}$R$^{12}$, or —C(O)NR$^{11}$R$^{12}$, where R$^{11}$ and R$^{12}$ are, independently, hydrogen, lower alkyl, substituted lower alkyl, aryl, substituted aryl, aryl(lower)alkyl, substituted aryl(lower)alkyl, heteroaryl(lower)alkyl, substituted heteroaryl(lower)alkyl, heterocyclyl, substituted heterocyclyl, heteroaryl, or substituted heteroaryl, or —C(O)OR$^{13}$ where R$^{13}$ is hydrogen or lower alkyl;

R$^2$ is hydrogen, lower alkyl, substituted lower alkyl, halo, hydroxyl, lower alkoxy, substituted lower alkyloxy, carboxyl, —NR$^{11}$R$^{12}$, —NR$^{11}$C(O)R$^{12}$, or —C(O)NR$^{11}$R$^{12}$, where R$^{11}$ and R$^{12}$ have the above meanings, or R$^2$ and R$^3$, together with the carbon atoms to which they are attached, form a heterocyclic ring;

R$^5$ is hydrogen, lower alkyl, substituted lower alkyl, or aryl;

R$^6$ and R$^7$ are, independently, hydrogen, lower alkyl or —C(O)OR$^{13}$, where R$^{13}$ has the above meaning;

R$^8$ and R$^9$ are, independently, hydrogen, lower alkyl, substituted lower alkyl, halo, hydroxyl, lower alkoxy, carboxyl, —NR$^{11}$R$^{12}$, or —C(O)N R$^{11}$R$^{12}$, where R$^{11}$ and R$^{12}$ have the above meanings, R$^{10}$ is hydrogen, lower alkyl, substituted lower alkyl, halo, hydroxy, lower alkoxy, —C(O)OR$^{13}$ where R$^{13}$ is hydrogen or lower alkyl, —SO$_3$H, or —C(O)NR$^{11}$R$^{12}$, where R$^{11}$ and R$^{12}$ have the above meanings;

and the pharmaceutically acceptable salts thereof; as single stereoisomers or mixtures of stereoisomers.

In a first preferred embodiment, R$^6$ is —C(O)OR$^{13}$. More preferably, R$^1$R$^4$ are independently hydrogen, hydroxyl, lower alkoxy, or substituted lower alkoxy such as OCH$_2$CO$_2$R$^{13}$or OCH$_2$PhCO$_2$R$^{13}$ in which Ph is phenylene. Certain compounds of this preferred embodiment are useful as intermediates to prepare other compounds of formula I with higher activity.

In a second preferred embodiment, R$^2$ is NR$^{11}$R$^{12}$ where R$^{11}$ and R$^{12}$ are independently hydrogen, lower alkyl, substituted lower alkyl, aryl, or substituted aryl. Certain compounds of this preferred embodiment are useful as intermediates to prepare other compounds of formula I with higher activity.

In a third preferred embodiment, R$^2$ is N(R$^{11}$)C(O)R$^{12}$ where R$^{11}$ and R$^{112}$ are independently hydrogen, lower alkyl, substituted lower alkyl, aryl, or substituted aryl. Certain compounds of this preferred embodiment are useful as intermediates to prepare other compounds of formula I with higher activity. Within this third preferred embodiment, more preferably, $R^{11}$ is hydrogen or lower alkyl and $R^{12}$ is 4-($R^{13}$-oxycarbonyl)phenyl. Certain compounds of these preferred embodiments are useful as intermediates to prepare other compounds of formula I with higher activity.

In a fourth preferred embodiment of the invention, $R^1$–$R^3$ and $R^6$–$R^9$ are independently hydrogen or lower alkyl, $R^4$ is —C(O)O$R^{13}$, and $R^{10}$ is lower alkyl or substituted lower alkyl. Certain compounds of this preferred embodiment are useful as intermediates to prepare other compounds of formula I with higher activity.

In a fifth preferred embodiment of the invention, $R^1$–$R^6$ and $R^8$–$R^{10}$ are independently hydrogen or lower alkyl, and $R^7$ is —C(O)O$R^{13}$. Certain compounds of this preferred embodiment are useful as intermediates to prepare other compounds of formula I with higher activity.

In a sixth preferred embodiment of the invention, $R^1$ and $R^4$–$R^9$ are hydrogen or lower alkyl, $R^2$ and $R^3$, together with the carbon atoms to which they are attached, form a heterocyclic ring, and $R^{10}$ is hydroxy or alkoxy. Certain compounds of this preferred embodiment are useful as intermediates to prepare other compounds of formula I with higher activity.

In a seventh preferred embodiment, $R^1$, $R^3$–$R^5$, and $R^7$–$R^9$ are hydrogen, $R^2$ is —NHCH$_3$, and $R^6$ is —CO$_2$H.

In a particularly preferred embodiment of the present invention, $R^1$, $R^3$, $R^4$, and $R^7$–$R^9$ are hydrogen, $R^2$ is —N(CH$_3$)C(O)(4-carboxyphenyl), $R^5$ is methyl, $R^6$ is —CO$_2$H, and $R^{10}$ is —CH$_2$CO$_2$H.

Compounds of the present invention include, but are not limited to, the following compounds:

5-((1E)-2-phenylvinyl)-2-({4-[(4-carboxyphenyl)-N-methylcarbonylamino]phenyl}-N-methyl carbonylamino)benzoic acid;
4-((1E)-2-{4-[(4-{[4-(methoxycarbonyl)phenyl]N-methylcarbonylamino}phenyl)-carbonyl amino]phenyl}vinyl)benzoic acid;
5-[(1E)-2-(4-carboxyphenyl)vinyl]-2-{[4-(methylamino)phenyl]carbonylamino}benzoic acid;
2-[N-(4-{(1E)-2-[4-(carboxymethyl)phenyl]vinyl}phenyl)carbamoyl]benzoic acid;
5-((1E)-2-phenylvinyl)-2-(N-methylphenylcarbonylamino) benzoic acid;
5-((1E)-2-phenylvinyl)-2-[(3,4,5-trimethoxyphenyl) carbonylamino]benzoic acid;
methyl 5-((1E)-2-phenylvinyl)-2-(phenylcarbonylamino) benzoate;
5-[(1E)-2-(4-methoxyphenyl)vinyl]-2-(N-methylphenylcarbonylamino)benzoic acid;
methyl 4-{N-[4-(N-{4-[(1E)-2-(4-methoxyphenyl)vinyl]-2-(methoxycarbonyl)phenyl}carbamoyl)phenyl]-N-methylcarbamoyl}benzoate;
5-[(1E)-2-(4-methoxyphenyl)vinyl]-2-[(4-{[4-(methoxycarbonyl)phenyl]N-methylcarbonyl amino}phenyl)carbonylamino]benzoic acid;
5-[(1E)-2-(4-methoxyphenyl)vinyl]-2-({4-[(4-carboxyphenyl)-N-methylcarbonylamino] phenyl}carbonylamino)benzoic acid;
methyl 4-{N-[4-(N-{4-[(1E)-2-(2-fluorophenyl)vinyl]-2-(methoxycarbonyl)phenyl}carbonyl)-phenyl]-N-methylcarbamoyl}benzoate;
5-[(1E)-2-(2-fluorophenyl)vinyl]-2-({4-[(4-carboxyphenyl)-N-methylcarbonyl-amino] phenyl}carbonylamino)benzoic acid;
methyl 4-{N-[4-(N-{4-[(1E)-2-(4-fluorophenyl)vinyl]-2-(methoxycarbonyl)phenyl}phenyl]-N-methylcarbamoyl}benzoate;
5-[(1E)-2-(4-fluorophenyl)vinyl]-2-({4-[(4-carboxyphenyl)-N-methylcarbonylamino] phenyl}carbonylamino)benzoic acid;
4-((1E)-2-{3-(methoxycarbonyl)-4-[(4-{[4-(methoxycarbonyl)phenyl]-N-methylcarbonyl amino}phenyl)carbonylamino]phenyl}vinyl) benzenesulfonic acid;
methyl 4-{N-[4-(N-{4-[(1E)-2-(3-fluorophenyl)vinyl]-2-(methoxycarbonyl)phenyl}carbonyl)phenyl]-N-methylcarbamoyl}benzoate;
2-((1E)-2-phenylvinyl)-5-(phenycarbonylamino)benzoic acid;
2-((1E)-2-phenylvinyl)-5-[(4-{[4-(methoxycarbonyl) phenyl]-N-methylcarbonylamino}phenyl) carbonylamino]benzoic acid;
methyl 4-[N-(4-{N-[4-((1E)-2-phenylvinyl)-2-(methoxycarbonyl)phenyl]-carbamoyl}phenyl)-N-methylcarbamoyl]benzoate;
5-((1E)-2-phenylvinyl)-2-[(3,5-dihydroxyphenyl) carbonylamino]benzoic acid;
5-((1E)-2-phenylvinyl)-2-[(3-methoxyphenyl) carbonylamino]benzoic acid;
5-((1E)-2-phenylvinyl)-2-({4-[(4 -carboxyphenyl)-N-methylcarbonylamino]phenyl}carbonyl amino)benzoic acid;
methyl 4-(N-{4-[N-(4-{(1E)-2-[4-(methoxycarbonyl) phenyl]vinyl}phenyl)-carbamoyl]phenyl}-N-methylcarbamoyl)benzoate;
2-[3-((1E)-2-{4-[(4-{[4-(methoxycarbonyl)phenyl]-N-methylcarbonylamino}phenyl)-N-methyl carbonylamino]phenyl}vinyl)phenyl]acetic acid;
2-[3-((1E)-2-{4-[(4-{[4-(methoxycarbonyl)phenyl]-N-methylcarbonylamino}phenyl)carbonyl amino]phenyl}vinyl)phenyl]acetic acid;
4-((1E)-2-{4-[(4-{[4-(methoxycarbonyl)phenyl]-N-methylcarbonylamino}phenyl)-N-methyl carbonylamino]phenyl}vinyl)benzoic acid;
methyl 4-(N-{4-[N-(4-{(1E)-2-[4-(methoxycarbonyl) phenyl]vinyl}phenyl)-N-methyl carbamoyl]phenyl}-N-methylcarbamoyl)benzoate;
5-((1E)-2-{4-[(4-{[4-(methoxycarbonyl)phenyl]-N-methylcarbonylamino}phenyl)-N-methyl carbonylamino]phenyl}vinyl)-2-(tert-butoxy)benzoic acid;
5-{(1E)-2-[4-({4-[(4-carboxyphenyl)-N-methylcarbonylamino]phenyl}-N-methylcarbonyl amino)phenyl]vinyl}-2-(tert-butoxy)benzoic acid;
5-{(1E)-2-[4-({4-[(4-carboxyphenyl)-N-methylcarbonylamino]phenyl}N-methylcarbonyl amino) phenyl]vinyl}-2-hydroxybenzoic acid;
methyl 5-((1E)-2-phenylvinyl)-2-[(3,4-dimethoxyphenyl) carbonylammo]benzoate;
5-((1E)-2-phenylvinyl)-2-[(3,4-dimethoxyphenyl) carbonylamino]benzoic acid;
5-((1E)-2-phenylvinyl)-2-[(3,5-dimethoxyphenyl) carbonylamino]benzoic acid;
2-{5-((1E)-2-phenylvinyl)-2-[(3-methoxyphenyl) carbonylamino]phenyl}acetic acid;
N-{4-[(1E)-2-(4-methoxyphenyl)vinyl]phenyl}-2H-benzo [d]1,3-dioxolen-5-ylcarboxamide;
5-[(1E)-2-(4-methoxyphenyl)vinyl]-2-(N-[(4-carboxyphenyl)methyl]{4-[(4-carboxyphenyl)-N-methylcarbonylamino]phenyl}carbonylamino)benzoic acid;

2-((1E)-2-phenylvinyl)-5-({4-[(4-carboxyphenyl)-N-methylcarbonylamino]phenyl} carbonyl amino)benzoic acid;

5-((1E)-2-phenylvinyl)-2-{[3,5-bis(carboxymethoxy)phenyl]carbonylamino}benzoic acid;

5-((1E)-2-phenylvinyl)-2-({3,5-bis[(4-carboxyphenyl)methoxy]phenyl}carbonylamino)benzoic acid; and 5-((1E)-2-phenylvinyl)-2-({3,5-bis[(3-carboxyphenyl)methoxy]phenyl}carbonylamino)benzoic acid, and pharmaceutically acceptable salts thereof.

A process for preparing the compounds is described below, and descriptions of these compounds are outlined in Examples 1–3, likewise below.

Certain compounds of the invention may contain one or more chiral centers. In such cases, all stereoisomers also fall within the scope of this invention. The invention compounds include the individually isolated stereoisomers as well as mixtures of such stereoisomers.

The compounds of the invention further comprise pharmaceutically acceptable salts of the compounds disclosed herein. These pharmaceutically acceptable salts are suitable for use in all methods and pharmaceutical compositions of the present invention.

Pharmaceutically acceptable salts include salts which may be formed when acidic protons present are capable of reacting with inorganic or organic bases. Typically, the parent compound is treated with an excess of an alkaline reagent, such as hydroxide, carbonate, or alkoxide, containing an appropriate cation. Cations such as $Na^+$, $K^+$, $Ca^{2+}$, and $NH_4^+$ are examples of cations present in pharmaceutically acceptable salts. The $Na^+$ salts are especially useful. Acceptable inorganic bases, therefore, include aluminum hydroxide, calcium hydroxide, potassium hydroxide, sodium hydroxide, and sodium carbonate. Salts may also be prepared using organic bases, such as ethanolamine, diethanolamine, triethanolamine, N-methylglucamine, and tromethamine.

If the compound of the invention contains a basic group, an acid addition salt may be prepared. Acid addition salts of the compounds are prepared in a standard manner in a suitable solvent from the parent compound and an excess of an acid, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluenesulfonic acid, hexanoic acid, heptanoic acid, cyclopentanepropionic acid, lactic acid, o-(4-hydroxy-benzoyl)benzoic acid, 1,2-ethanedisulfonic acid, 2-hydroxyethanesulfonic acid, benzenesulfonic acid, p-chlorobenzenesulfonic acid, 2-naphthalenesulfonic acid, camphorsulfonic acid, 4-methyl-bicyclo-[2.2.2]oct-2-ene-1-carboxylic acid, glucoheptonic acid, gluconic acid, 4,4'-methylenebis(3-hydroxy-2-naphthoic)acid, 3-phenylpropionic acid, trimethylacetic acid, t-butylacetic acid, laurylsulfuric acid, glucuronic acid, glutamic acid, 3-hydroxy-2-naphthoic acid, stearic acid, muconic acid and the like.

Certain of the compounds of the invention form inner salts or zwitterions.

Pharmaceutical compositions of all of the compounds in the present invention are contemplated. These pharmaceutical compositions comprise (i) a compound of the invention as an active ingredient and (ii) at least one pharmaceutically acceptable carrier.

Pharmaceutical compositions of the compounds of this invention, or derivatives thereof, may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, 5% dextrose in water or buffered sodium or ammonium acetate solution. Such formulations are especially suitable for parenteral administration, but may also be used for oral administration. It may be desirable to add excipients such as polyvinylpyrrolidinone, gelatin, hydroxycellulose, acacia, polyethylene glycol, mannitol, sodium chloride, or sodium citrate. Alternatively, these compounds may be encapsulated, tableted, or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate dihydrate, terra alba, magnesium stearate or stearic acid, talc, pectin, acacia, agar, or gelatin. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The amount of a compound of formula I in the composition may vary widely, depending on the type of composition, size of unit dosage, kind of excipient(s), and other factors known to those skilled in the art of pharmaceutical sciences. In general, the final composition will comprise from 1% w/w to 99% w/w, more preferably, 10% w/w to 90% w/w, most preferably 25% w/w to 75% w/w of the compound, with the remainder being the excipient or excipients.

Preferred compositions will include preferred compounds identified.

Some specific examples of suitable pharmaceutical compositions are described in Examples 7–9 below.

Typically, a pharmaceutical composition of the present invention would be packaged in a container with a label indicating use of the pharmaceutical composition in the treatment of hyperglycemia, Type I diabetes, and Type II diabetes, or a combination of any of these disease conditions.

(c) Preferred Methods of Use of the Compounds of the Present Invention.

Another aspect of the invention is directed towards methods of treatment administering the compounds of formula I or pharmaceutically acceptable salts thereof to a mammalian host. Preferred methods incorporate the administration of the preferred compounds identified.

Compounds of the present invention have been found to stimulate autophosphorylation of the insulin receptor (Example 5 below). In addition, these compounds have been shown to enhance insulin's ability to effect the transport of glucose into cultured fibroblast cells (Example 6 below).

The ability of the compounds of this invention to stimulate autophosphorylation of the insulin receptor and to stimulate the uptake of glucose into cells, which is demonstrated in the specific examples, Examples 5 and 6 below, indicates their usefulness in the treatment and management of subjects with diabetes. Without intending to be bound by any theory, it is believed that the compounds of the invention act directly on the kinase function of the insulin receptor and do not necessarily compete with insulin for binding at the insulin-binding site, nor do they effect activation of the receptor by a mechanism similar to that exhibited by insulin. Thus, they are able directly to activate the kinase to autophosphorylate, to potentiate the effect of insulin, to activate the kinase function of the receptor in phosphorylating exogenous substrates and to effect the increased uptake of glucose by adipocytes and insulin receptor-bearing cells in general and to lower blood glucose in diabetic subjects. Accordingly, by virtue of the activities of the compounds of the invention, they may be used to stimulate the kinase activity of an insulin receptor, to enhance the activation of the insulin receptor by insulin, to enhance the stimulation by insulin of cellular glucose uptake, and to stimulate the uptake of glucose in diabetic subjects. Thus, the compounds of this invention are useful in the treatment of hyperglycemia and diabetes in mammals.

One aspect of the invention is directed to a method of stimulating the kinase activity of the insulin receptor. This method comprises contacting the insulin receptor, or the kinase portion thereof, with a compound of the invention in an amount sufficient to stimulate the kinase activity of the insulin receptor. By stimulating the kinase activity of the insulin receptor, both autophosphorylation and phosphorylation of exogenous substrates is enhanced. The stimulation of the kinase activity of the insulin receptor may occur either in vivo or in vitro. The method of stimulating the kinase activity of the insulin receptor may optionally further comprise contacting the insulin receptor with insulin.

In another embodiment of the invention, the insulin receptor is activated by contacting the insulin receptor, or the kinase portion thereof, with a compound of the invention in an amount sufficient to activate the insulin receptor. The targeted insulin receptor may optionally be on the surface of a cell in a mammal. In such a case, the contacting is effected by administering the compound, or a pharmaceutical composition thereof, to the mammal. Optionally, the method may further comprise contacting the insulin receptor with insulin.

In an alternative embodiment, the compounds of the invention are used to stimulate the uptake of glucose into cells displaying the insulin receptor. This method comprises contacting the cells in vitro or in vivo with a compound of the invention, optionally in the presence of insulin, and in an amount sufficient to stimulate the uptake of glucose into the cells. The targeted cells may optionally be in a mammal and the step of contacting the receptor with the compound may then be effected by administering the compound, or pharmaceutical composition thereof, to the mammal. In one embodiment of the method of stimulating the uptake of glucose into cells displaying the insulin receptor, the cells are also contacted with exogenous insulin.

A method of treating hyperglycemia or another disease involving an imbalance of glucose levels in a mammal, preferably a human, is also contemplated by the present invention. The method comprises administering a therapeutically effective amount of a compound of this invention, or a pharmaceutical composition thereof, to a mammnal. Optionally, the method may further comprise treating the mammal with one or more additional forms of therapy or treatment for hyperglycemia. For instance, one method may comprise administering exogenous insulin to the mammal in addition to the compound of the invention. Alternatively, the compounds of the invention may be administered to the mammal in combination with a non-insulin drug or other alternative treatment for hyperglycemia. The total amount of the combination of drugs administered to the mammal must be a therapeutically effective amount, although the amounts of each of the individual drugs may by themselves be sub-optimal for therapeutic purposes, and in particular the amount of insulin or the non-insulin drug or other alternative treatment for hyperglycemia or the other disease may be subtherapeutic if administered alone.

In one embodiment of the invention, the compounds are used to treat type I diabetes in a mammal. This method comprises administering a therapeutically effective amount of a compound of this invention, or a pharmaceutical composition thereof, to the mammal. In a preferred embodiment, the mammal is a human. The method of treating type I diabetes may optionally further comprise treating the mammal with one or more additional therapies or treatments for type I diabetes. For instance, in one embodiment of the method of treating type I diabetes, a compound of the invention and insulin may both be administered to the mammal. Alternatively, the additional form of treatment for type I diabetes which is combined with administration of the compound of the invention may be an antidiabetic agent other than insulin or another alternative form of treatment for type I diabetes. Again, the total amount of the combination of antidiabetic agents administered to the mammal must be a therapeutically effective amount, although the amounts of each of the individual drugs may be sub-optimal for therapeutic purposes if those drugs were to be delivered alone to the mammal with type I diabetes, and in particular the amount of insulin or the non-insulin drug or other antidiabetic agent or alternative treatment for type I diabetes may be subtherapeutic if administered alone.

In another embodiment of the invention, the compounds are used to treat type II diabetes in a mammal. This method comprises administering a therapeutically effective amount of a compound of this invention, or a pharmaceutical composition thereof, to the mammal. Again, the preferred subject is a human.

Again, like the other treatment methods of the invention, this method may farther comprise treating the mammal with one or more additional forms of therapy or treatment for type II diabetes, such as administering insulin to the mammal. The insulin is delivered to the mammal in an amount which is therapeutically effective when used in conjunction with a compound of the invention. This therapeutically effective amount of insulin when used in combination with a compound of the invention may be less than the amount of insulin which would be therapeutically effective if delivered to the mammal alone. It is understood that the insulin which is administered in any of the treatments of the present invention may either be isolated from a natural source or be recombinant. In addition, an insulin analog may be substituted for insulin in any of the treatments of the present invention.

Use of the compounds of the invention for treating type II diabetes by combination may also comprise the administration of the compound of the invention to the mammal in combination with a non-insulin antidiabetic agent or other treatment for type II diabetes. For instance, the antidiabetic drug which is administered to the mammal in combination with a compound of the invention may optionally be a thiazolidinedione, such as troglitazone, or a sulfonylurea. The total amount of the combination of drugs (invention compound plus insulin and/or other antidiabetic drug) administered to the mammal for the treatment of type II diabetes must be a therapeutically effective amount, although the amounts of each of the individual drugs used in the combination therapy may be sub-optimal for therapeutic purposes if those drugs were to be delivered alone to the mammal with type II diabetes, and in particular the amount of the non-insulin antidiabetic agent or other treatment for type II diabetes may be subthetapeutic if administered alone.

This invention also includes a method of obtaining and/or developing a compound that has the function of stimulating the kinase activity of the insulin receptor, activating the insulin receptor, and/or stimulating the uptake of glucose, by using a compound of this invention as a model. It also includes a method for identifying a compound which mimics the function of a compound of this invention, by submitting a test compound to a screen for determining its stimulation of the kinase activity of the insulin receptor relative to a compound of the invention; and identifying the test compound as one which mimics the function of a compound of this invention if it exhibits stimulation of the kinase activity of the insulin receptor. Another aspect of the invention is directed to a method for validating, optimizing, or standardizing a bioassay, comprising using a compound of this invention as a standard. A radiolabelled compound of this invention is also contemplated.

The compounds of this invention are, thus, used to enhance glucose uptake in patients which require such treatment. The method of treatment comprises administration parenterally and orally of a therapeutically effective quantity of the chosen compound of the invention, preferably dispersed in a pharmaceutical carrier. Dosage units of the active ingredient are generally selected from the range of 0.01–1000 mg/kg, preferably 0.01–100 mg/kg and more preferably 0.1–50 mg/kg. but will be readily determined by one skilled in the art depending upon the route of administration, age, and condition of the patient. The compounds of the invention are most preferably administered in a dosage unit of 1–10 mg/kg. These dosage units may be administered one to ten times daily for acute or chronic disease. No unacceptable toxicological effects are expected when compounds of the invention are administered in accordance with the present invention.

The invention compounds may be administered by any route suitable to the subject being treated and the nature of the subject's condition. Routes of administration include, but are not limited to, administration by injection, including intravenous, intraperitoneal, intramuscular, and subcutaneous injection, by transmucosal or transdermal delivery, through topical applications, nasal spray, suppository and the like, or may be administered orally. Formulations may optionally be liposomal formulations, emulsions, formulations designed to administer the drug across mucosal membranes, or transdermal formulations. Suitable formulations for each of these methods of administration may be found, for example, in *Remington: The Science and Practice of Pharmacy*, A. Gennaro, ed., 20th edition, Lippincott, Williams & Wilkins, Philadelphia, Pa.

Processes for the preparation of the compounds of formula I comprise another aspect of the invention. Preferred processes generate the preferred compounds identified. In one embodiment of the invention, a compound of Formula I or a pharmaceutically acceptable salt thereof, can be prepared by a process comprising:

(a) reaction of an iodo-amide compound of the formula

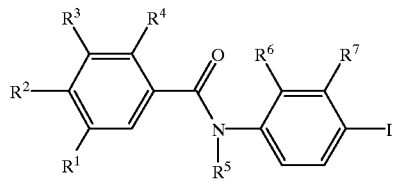

where $R^1$–$R^7$ are as defined above,
with a styrene or substituted styrene of the formula

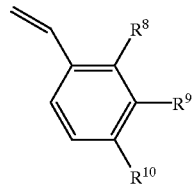

where $R^8$–$R^{10}$ are as defined above; or
(b) acylation of an aminostilbene of the formula

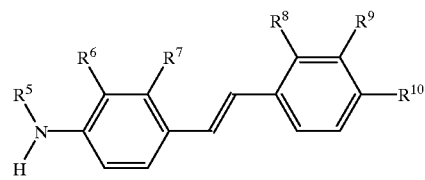

where $R^5$–$R^{13}$ are as defined above,
with a compound of the formula

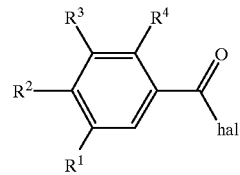

where hal is chlorine or bromine, and $R^1$–$R^4$ and $R^{11}$–$R^{13}$ are as defined above; or
(c) chemical elaboration of one or more substituents $R^1$–$R^{10}$ where said substituent is convertible into another substituent $R^1$–$R^{10}$; or
(d) introduction of a substituent $R^1$–$R^{10}$ into one, two or all three of the phenyl rings; or
(e) deprotection of a protected group; or
(f) salt formation or interconversion; or
(g) ester or amide hydrolysis; or
(h) liberation of a free acid or base of a compound of Formula I, where $R^1$–$R^{12}$ are as defined above; or
(i) stereoisomer separation or synthesis.

The reaction of the iodo-amide compound with the styrene or substituted styrene shown in (a), above, can be carried out between 40° C. and 120° C. in the presence of such solvents as DMF, toluene, methylene chloride, or the like.

Chemical elaboration of one or more substituents $R^1$–$R^{10}$ via the conversion of one such substituent into another substituent may be accomplished via hydrolysis, salt formation, acidification, alkylation, esterification, oxidation, or reduction.

In hydrolysis, an ester or amide compound is dissociated by reaction with water. Hydrolysis is catalyzed by acid or base, and hydrolysis of an amide generally requires more vigorous conditions (for example, a higher concentration of sulfuric acid at 1–100° C. for 1–5 hours) than those required for the hydrolysis of esters. Hydrolysis reactions can also be carried out with aqueous hydrochloric acid at 100–150° C. and may require as long as 18 hours.

In salt formation, a free acid is converted into a salt via addition of a basic reagent, such as aqueous sodium hydroxide or triethanolamine, that replaces all or part of the hydrogen ions of the acid with one or more cations of a base. The conversion of a compound into its corresponding acid addition salt is accomplished via treatment with a stoichiometric amount of an appropriate acid, such as hydrochloric acid. Typically, the free base is dissolved in a polar organic solvent, such as methanol or ethanol, and the acid is added in methanol or ethanol. The temperature is maintained at 0–50° C. The corresponding salt precipitates spontaneously or can be brought out of solution with a less polar solvent. In acidification, a chemical compound is converted into an acid.

In alkylation, an alkyl group is added to or substituted in a compound. Alkylation is carried out in a suitable solvent, such as acetonitrile, DMF, or THF, at 0–160° C., typically at approximately 25° C. to reflux, over approximately 1–18 hours.

An esterification reaction results in the formation of at least one ester product. In brief, the compound is reacted with from 1–5, preferably 2, molar equivalents of an alkanol, a thiol or ammonia, a monoalkylamine, or dialkylamine, or a heterocyclic aminoalkanol, optionally in the presence of from 1–1.5, preferably 1.25, molar equivalents of a tertiary organic base such as 4-dimethylaminopyridine or, preferably, triethylamine, in an organic solvent such as dioxane, tetrahydrofuran, or, preferably, dichloromethane. The reaction takes place between −10° C. and 50° C., preferably at ambient temperature, for 1–24 hours, preferably 4 hours.

EXAMPLES

The Examples which follow serve to illustrate this invention. The Examples are in no way intended to limit the scope of this invention, but are provided to show how to make and use the compounds of this invention.

The compounds of this invention are prepared by standard methods of organic chemistry. hi some cases, protective groups may be introduced and finally removed. Suitable protective groups for amino, hydroxyl, and carboxyl groups are described in Greene, et al. "Protective Groups in Organic Synthesis," Third Edition, John Wiley and Sons, New York, 1999. Activation of carboxylic acid can be achieved by using a number of different reagents as described in Larock, "Comprehensive Organic Transformations", VCH Publishers, New York, 1989.

The synthesis of the inventive compounds consists of the preparation of certain carboxybenzanilides 1a, 1b having an unprotected carboxylic acid, and aminostilbenes 3 which are then joined together. For example, when the convergent reaction is an amidation, the carboxybenzanilide is converted to the corresponding acyl chloride 2a or 2b and then condensed with an aminostilbene 3, as illustrated in Scheme 1.

Scheme 1

An aminostilbene of the formula

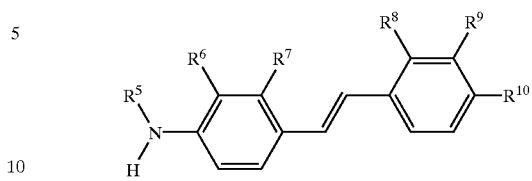

where $R^5$–$R^{13}$ are as defined above, is acylated with a compound of the formula

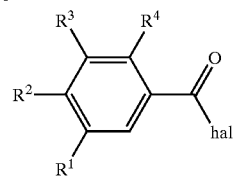

where hal is chlorine or bromine, and $R^1$–$R^4$ and $R^1$–$R^{13}$ are as defined above; or an acylation is carried out to elaborate the $R^2$ group, when $R^2$ is —$NR^{11}C(O)R^{12}$ or —$C(O)NR^{11}R^{12}$.

More specifically,

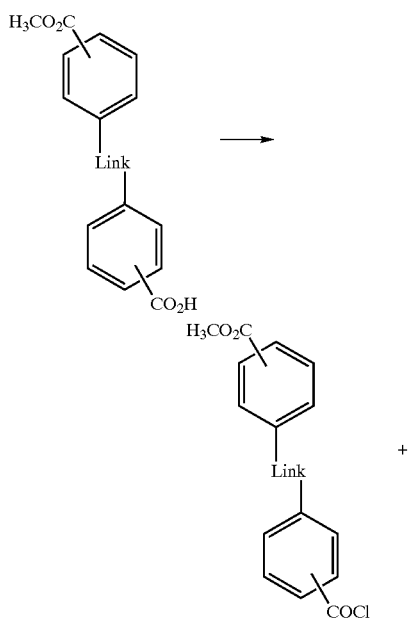

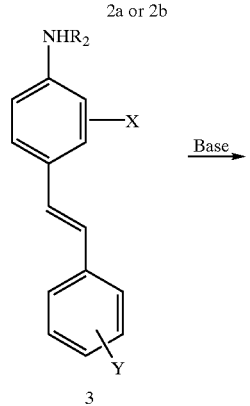

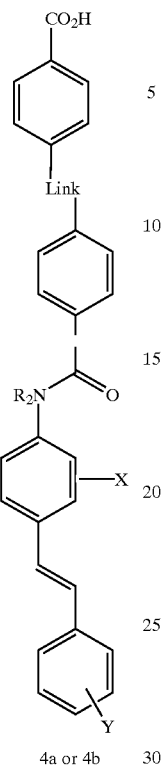

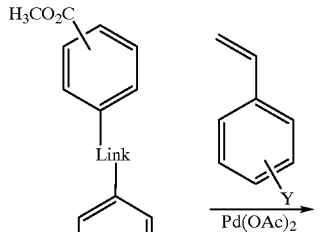

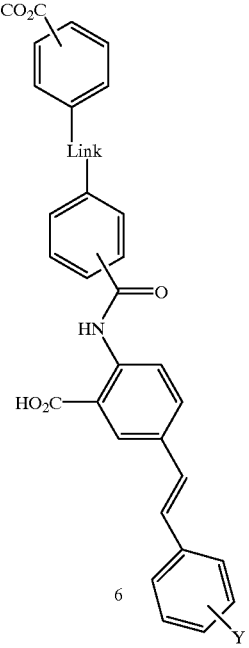

5 Link = —CONH—

$R_2$ corresponds to $R^5$; $R_1$ corresponds to $R^{11}$; X can be $R^6$ or $R^7$ or two independent substituents $R^6$ and $R^7$; and Y can be $R^8$, $R^9$, $R^{10}$, or three independent substituents $R^8$, $R^9$, and $R^{10}$. An alternate sequence for the assembly of the title compounds involves the condensation of the acyl chlorides 2a, 2b with 2-amino-5-iodobenzoic acid to give the iodo-amide 5. The final ring is then appended by a palladium catalyzed vinylation reaction using a styrene or substituted styrene as shown in Scheme 2.

Scheme 2

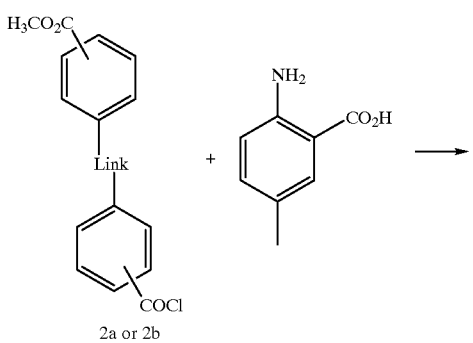

Synthesis of Carboxybenzanilides (2a, 2b)

Carboxybenzanilides with one free carboxylic acid are one of the components used in the assembly of the title compounds and the synthesis of these intermediates is shown in Schemes 3 and 4. Mono-methyl terephthalate was converted to the corresponding acyl chloride by reaction with oxalyl chloride. This acyl chloride was reacted with benzyl 4-aminobenzoate to give the benzanilide 8, which on hydrogenation gave the corresponding free carboxylic acid 9. The N-methyl amide was prepared by alkylation with methyl iodide in the presence of sodium hydride followed by hydrogenation to give 10. A shorter synthesis of 10 involved the acylation of 4-methylaminobenzoic acid with the acid chloride derived from mono-methyl terephthalate.

Scheme 3

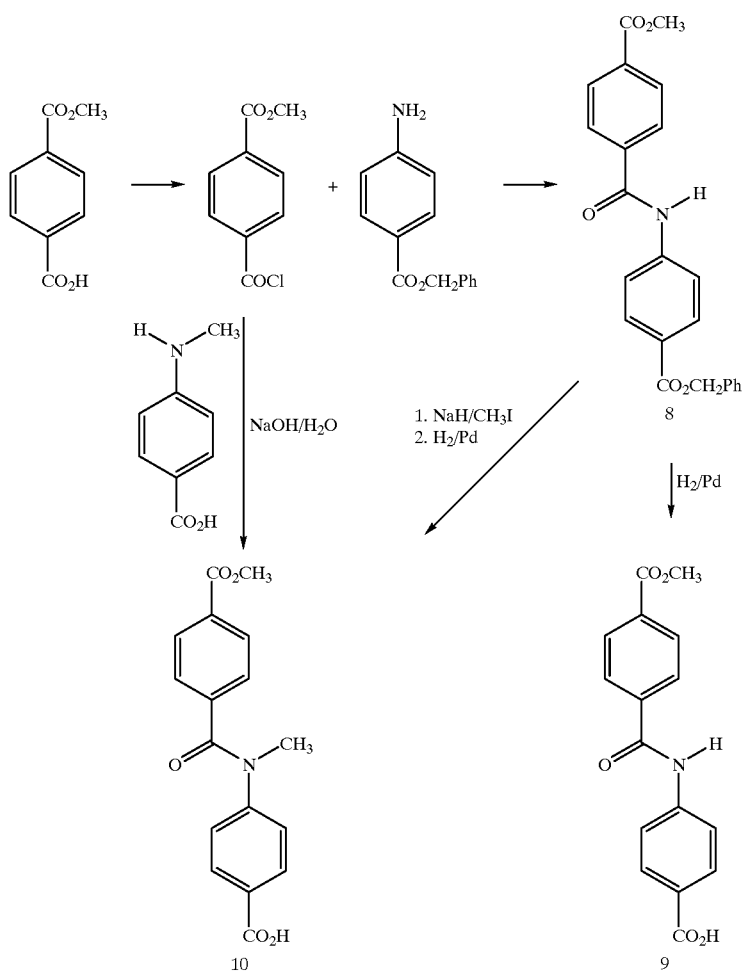

The isomeric carboxybenzanilide 11 was obtained by a similar sequence using mono-methyl isophthalate as the starting material as shown in Scheme 4.

Scheme 4

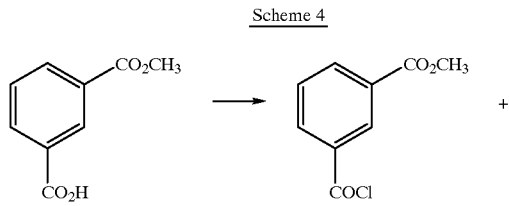

-continued

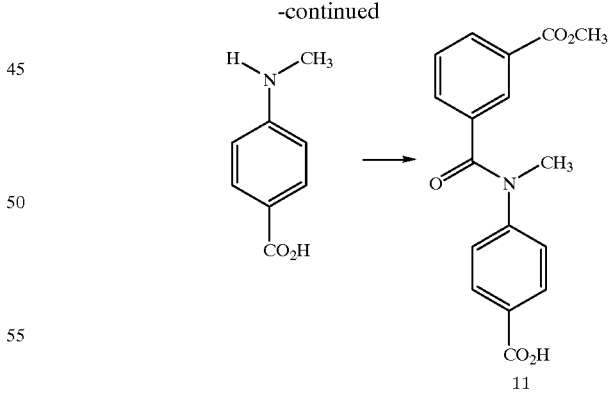

Synthesis of Aminostilbenes (3)

The second type of component used in the preparation of the title compounds is an aminostilbene. These intermediates were prepared by palladium(0) catalyzed vinylation of bromo-acetanilides such as 2-acetamido-5-bromobenzoic acid to give 12 as shown in Scheme 5. The carboxylic acid was protected as a methyl ester (13) and the acetyl group removed to give the aniline 14.

Scheme 5

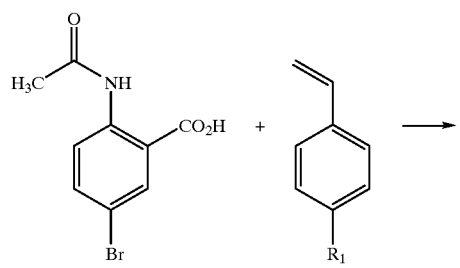

Scheme 6

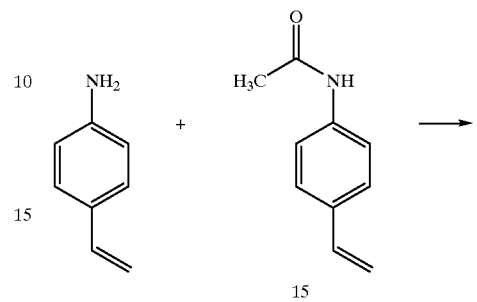

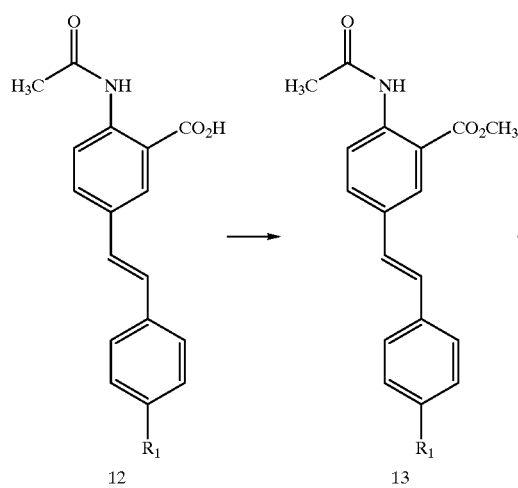

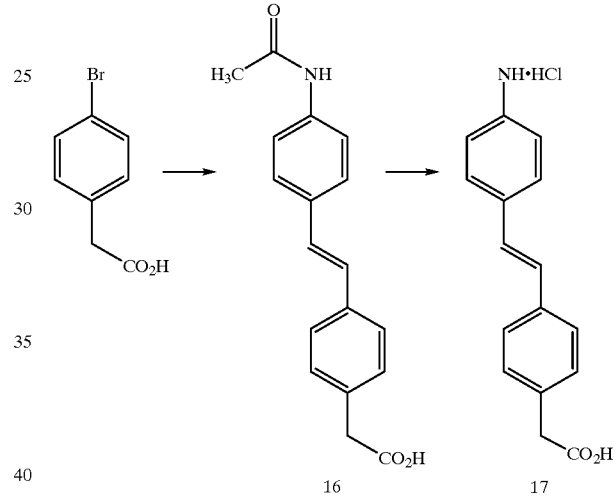

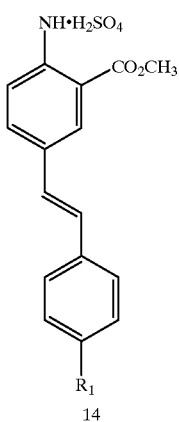

14

Aminostilbenes having an acetic acid side chain were synthesized by the sequence shown in Scheme 6 where 4-vinylacetanilide is arylated with 4-bromophenyl acetic acid to give 16 which was hydrolyzed with aqueous hydrochloric acid to the corresponding aniline 17.

Aminostilbenes having two carboxylic acid groups were prepared by the vinylation of 2-acetamido-5-bromobenzoic acid with, for example, 4-vinylbenzoic acid to give 18. This compound was then esterified and deacetylated to give the aniline 19 (Scheme 7).

Scheme 7

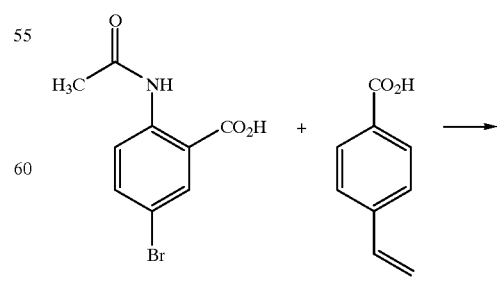

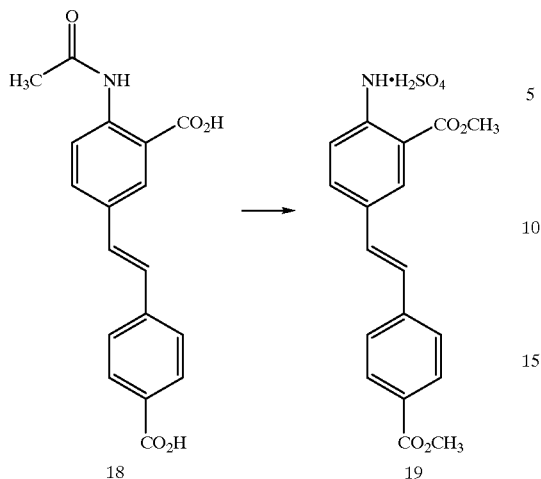

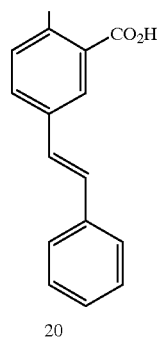

Amidation of Aminostilbenes

The synthesis of the title compounds involves the amidation of the of the aminostilbenes with the carboxybenzanilides followed in some cases by removal of the methyl ester protecting groups. For example, Scheme 8 shows the conversion of carboxyanilide 10 to the corresponding acyl chloride which is condensed with the aminostilbene 14 to give following hydrolysis of the ester functions the amide 20.

A second example in Scheme 9 is the condensation of the same acyl chloride with aminostilbene 17 to give the amide 21.

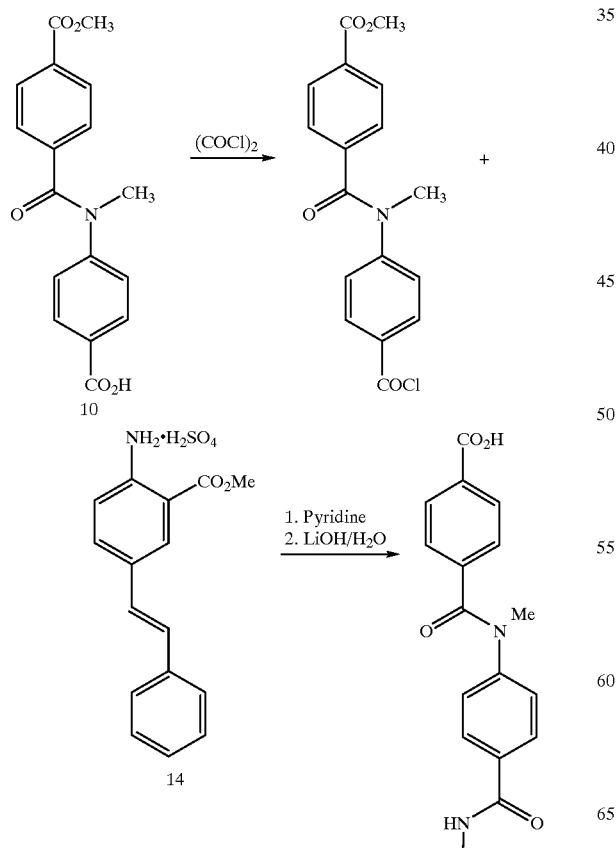

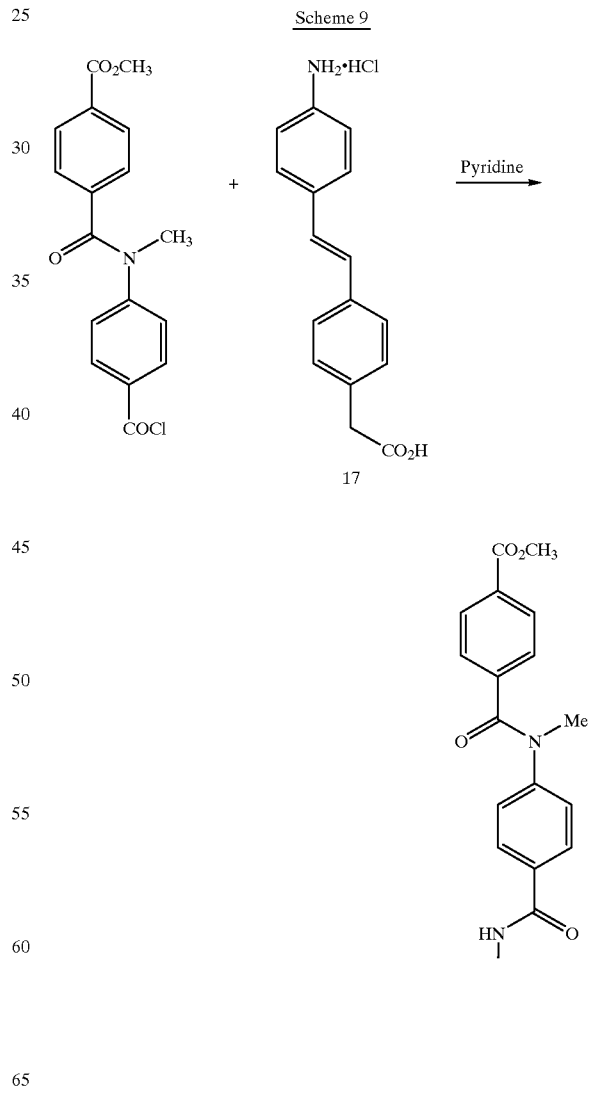

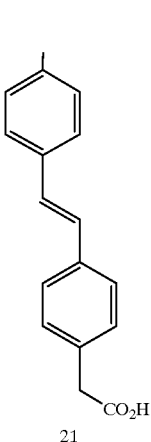

21

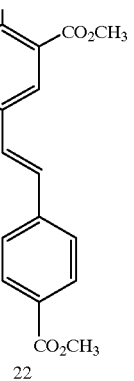

22

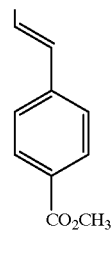

23

In Scheme 10, the same acid chloride is condensed with aminostilbene 19 to give amide 22. Upon treatment with excess aqueous sodium hydroxide this intermediate was converted to the dicarboxylic acid 23 which has the terephthaloyl group removed.

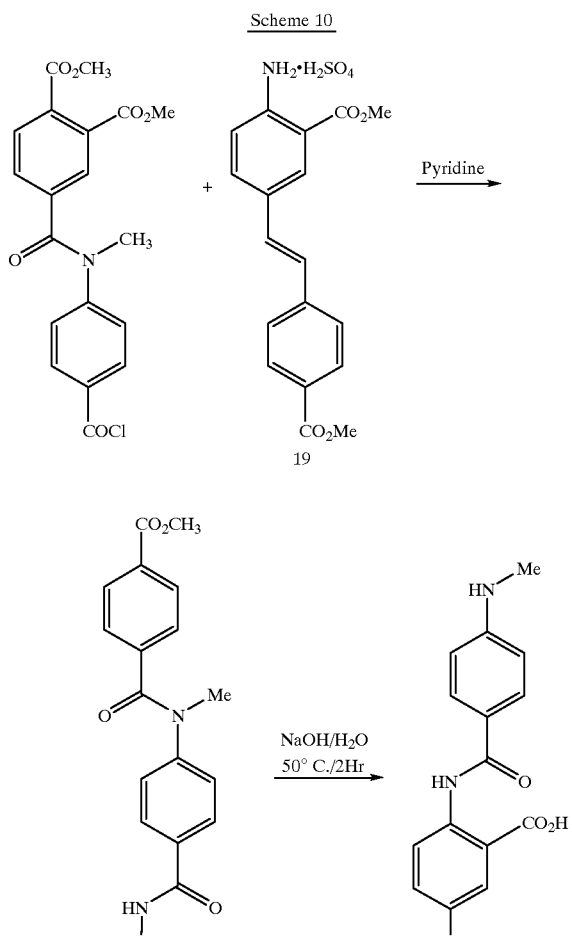

Scheme 10

The compounds of the invention can be synthesized as shown in the following examples.

Example 1

Synthesis of Compound 20

Preparation of Phenylmethyl 4-{[4-(methoxycarbonyl)phenyl]carbonylamino}benzoate (Compound 8)

A solution of mono-methyl terephthalate (4.00 g, 22 mmol) in ethyl acetate (25 mL) and DMF (0.1 mL) was cooled in an ice bath and treated with oxalyl chloride (11 mL, 2N in $CH_2Cl_2$, 22 mmol) over 30 minutes. After stirring 2 hours at room temperature the solvent was removed on a rotary evaporator and the residue dissolved in $CH_2Cl_2$ (20 mL) and added to a solution of benzyl 4-aminobenzoate (5.00 g, 22 mmol) in $CH_2Cl_2$ (25 mL) and triethylamine (4.3 mL, 31 mmol) at −60° C. The reaction mixture was warmed to room temperature for 1 hour and then partitioned between water and ethyl acetate. The ethyl acetate layer was dried over sodium sulfate, filtered, and evaporated. The residue was recrystallized from t-butyl methyl ether to give 5.85 g of compound 8.

Preparation of 4-[{4-(Methoxycarbonyl)phenyl]carbonylamino}benzoic Acid (Compound 9)

A solution of compound 8 (0.50 g, 1.30 mmol) in 1-propanol (30 mL) was treated with 10% Pd/C (0.30 g) and hydrogenated at 40 psi for 5 hours. The catalyst was removed by filtration and evaporation of the solvent gave 0.30 g of the carboxylic acid 9.

Preparation of 4-{[4-(Methoxycarbonyl)phenyl]-N-methylcarbonylamino}benzoic Acid (Compound 10)

Mono-methyl terephthalate (18.00 g, 0.10 mol) was converted to the corresponding acid chloride as described above and then dissolved in dioxane (35 mL). A solution of NaOH (4.00 g, 0.10 mol), water (500 mL) and 4-(methylamino)benzoic Acid (15.1 g, 0.10 mol) was cooled to 0° C. and treated by simultaneous addition over 45 minutes with the acid chloride solution and aqueous NaOH (4.00 g, 0.10 mol, in 50 mL of water). The reaction mixture was allowed to warm to room temperature over 2 hours and the treated with HCl (100 mL, 1 N). The product was extracted with ethyl acetate and recrystallized from the same solvent to give 19.41 g of compound 10.

Preparation of 5-((1E)-2-phenylvinyl)-2-(acetylamino)benzoic Acid (Compound 12)

A solution of 2-acetamido-5-bromobenzoic acid (2.05 g, 7.94 mmol), styrene (1.02 mL, 8.9 mmol), acetonitrile (20 mL) and triethylamine (10 mL) was treated with tritolylphosphine (0.365 g, 1.2 mmol) and Pd(OAc)$_2$ (0.055 g, 0.25 mmol). The reaction mixture was heated at 80° C. for 17 hours then cooled, diluted with water (30 mL) and filtered. The filtrate was washed twice with ether, cooled on ice and then acidified with HCl (2 ml, 12N). The solid product was collected by filtration and dried to give 2.34 g of compound 12.

Preparation of methyl 5-((1E)-2-phenylvinyl)-2-(acetylamino)benzoate (Compound 13)

A mixture of compound 12 (1.80 g, 6.40 mmol), dimethylformamide (8 mL), potassium carbonate (1.104 g, 8 mmol) and methyl iodide (0.62 mL, 10 mmol) was stirred 16 hours at room temperature and then poured into ice water. Extraction with CH$_2$Cl$_2$ followed by recrystallization from ethyl acetate gave 1.37 g of compound 13.

Preparation of Methyl 5-((1E)-2-phenylvinyl)-2-aminobenzoate (Compound 14)

The ester 13 (1.00 g, 3.39 mmol) in methanol (10 ml) was treated with sulfuric acid (0.27 ml, concentrated) and heated 4 hours at 60° C. The reaction mixture was cooled on ice and the product collected (0.958 g) by filtration. This product contained some starting material which was removed by silica gel chromatography eluting with ethyl acetate/hexane to give 0.61 g of compound 14.

Preparation of 2-((1E)-2-Phenylvinyl)-5-[(4-{[4-(methoxycarbonyl)phenyl]-N-methylcarbonyl amino}phenyl)carbonylamino]benzoic Acid (Compound 39)

The mono acid 10 (0.200 g, 0.64 mmol) was converted to the corresponding acid chloride as described above. A mixture of aminostilbene 14 (0.185 g, 0.64 mmol) and triethylamine (0.18 mL, 1.28 mmol) in dioxane (5 mL) was heated to 110° C. and the acid chloride was added. After 30 minutes the reaction mixture was cooled and diluted with water. The product was extracted with ethyl acetate and chromatographed on silica gel eluting with CH$_2$Cl$_2$/methanol mixtures to give 0.17 g of the dimethyl ester compound 39.

Preparation of 5-((1E)-2-Phenylvinyl)-2-({4-[(4-carboxyphenyl)-N-methylcarbonylamino]phenyl}-N-methylcarbonylamino)benzoic Acid (Compound 20)

Compound 39, 0.17 g, was dissolved in methanol (5 mL) and treated with lithium hydroxide (39 mg in 1 mL water). The reaction mixture was stirred at room temperature for 16 hours and then heated at 50° C. for 2 hours. After cooling on ice the reaction mixture was diluted with water and acidified with HCl. Extraction with ethyl acetate gave a crude product which was purified by silica gel chromatography eluting with CH$_2$Cl$_2$/methanol mixtures to give 0.062 g of compound 20.

Example 2

(Synthesis of Compound 21

Preparation of N-(4-Vinylphenyl)acetamide (Compound 15)

A solution of 4-vinylaniline (3.5 mL, 30 mmol) was prepared in aqueous HCl (30 mL, 2N). A solution of sodium acetate (35 g in 110 mL of water) was added and the resulting suspension was cooled on ice and treated with acetic anhydride (35 mL). After stirring 45 minutes the precipitate was collected by filtration and recrystallized from water to give 3.78 g of compound 15.

Preparation of 2-(4-{(1E)-2-[4-(Acetylamino)phenyl]vinyl}phenyl)acetic Acid (Compound 16)

A solution of 4-bromophenylacetic acid (1.72 g, 8.0 mmol), compound 15 (1.43 g, 8.8 mmol)), acetonitrile (23 mL) and triethylamine (10 mL) was treated with tritolylphosphine (0.365 g, 1.2 mmol) and Pd(OAc)$_2$ (0.055 g, 0.25 mmol). The reaction mixture was heated at 80° C. for 18 hours. The reaction mixture was cooled, treated with water (30 mL) and filtered. The filtrate was washed twice with ether, cooled on ice and then acidified with HCl (2 ml, 12N). The solid product was collected by filtration and dried to give 2.50 g of compound 16.

Preparation of 2-{4-[(1E)-2-(4-Aminophenyl)vinyl]phenyl}acetic Acid (Compound 17)

A suspension of 16 (2.183 g, 7.4 mmol) in water (24 mL), HCl (6 mL, 12 N) and dioxane (45 mL) was heated at 95° C. for 1 hour. The reaction mixture was cooled on ice and the resulting precipitate was collected and dried to give 1.17 g of compound 17.

Preparation of 4-((1E)-2-{4-[(4-{[4-(methoxycarbonyl)phenyl]-N-methylcarbonylamino}phenyl)carbonylamino]phenyl}vinyl)benzoic Acid (Compound 21).

The mono acid 10 (0.200 g, 0.64 mmol) was converted to the corresponding acid chloride as described above. A mixture of aminostilbene 17 (0.185 g, 0.64 mmol) in pyridine (5 mL) was cooled on an ice bath and the acid chloride in CH$_2$Cl$_2$ (4 mL) was added. After 10 minutes the reaction mixture was allowed to warm to room temperature for 90 minutes. The reaction mixture was diluted with water and the product was extracted with ethyl acetate and then chromatographed on silica gel eluting with CH$_2$Cl$_2$/ethyl acetate/acetic acid mixtures to give 43 mg of compound 21.

Example 3

(Synthesis of Compound 23).

Preparation of 5-[(1E)-2-(4-carboxyphenyl)vinyl]-2-(acetylamino)benzoic Acid (Compound 18)

A solution of 2-acetamido-5-bromobenzoic acid (2.06 g, 8 mmol), 4-vinylbenzoic acid (1.31 g, 8.8 mmol)), acetonitrile (25 mL) and triethylamine (10 mL) was treated with tritolylphosphine (0.365 g, 1.2 mmol) and Pd(OAc)$_2$ (0.055 g, 0.25 mmol). The reaction mixture was heated at 75° C. for 16 hours. The reaction mixture was cooled, treated with water (20 mL) and filtered. The filtrate was washed twice with ether, cooled on ice and then acidified with HCl (3 ml, 12N). The solid product was collected by filtration and dried to give 18 (2.20 g).

Preparation of Methyl 4-{(1E)-2-[4-amino-3-(methoxycarbonyl)phenyl]vinyl}benzoate (Compound 19)

A suspension of 18 (2.71 g, 6.8 mmol) in methanol (25 mL) was treated with sulfuric acid (2 mL, concentrated) and heated at 70° C. for 4 hours. The reaction mixture was evaporated and the residue recrystallized from ethyl acetate to give a methyl ester (2.05 g). This mono ester was suspended in methanol (20 mL) and sulfuric acid (1.0 mL), refluxed for 48 hours then cooled and the precipitate collected by filtration. Chromatography of this solid on silica gel eluting with CH$_2$Cl$_2$./methanol mixtures gave 0.49 g of compound 19.

Preparation of 5-[(1E)-2-(4-Carboxyphenyl)vinyl]-2-{[4-(methylamino)phenyl]carbonyl amino}benzoic Acid (Compound 23)

The mono acid 10 (0.200 g, 0.64 mmol) was converted to the corresponding acid chloride as described above. A mixture of aminostilbene 19 (0.262 g, 0.64 mmol) and triethylamine (0.18 mL, 1.28 mmol) in dioxane (5 mL) was heated to 100° C. and the acid chloride was added. After 20 minutes the reaction mixture was cooled and diluted with water. The product was extracted with ethyl acetate and chromatographed on silica gel eluting with CH$_2$Cl$_2$./ methanol mixtures to give the dimethyl ester of 22 (0.300 g). The dimethyl ester was dissolved in methanol (10 mL) and treated with aqueous sodium hydroxide (0.112 g in 2 mL water). The reaction mixture was stirred at room temperature for 16 hours and then heated at 50° C. for 2 hours. After cooling on ice the reaction mixture was diluted with water and acidified with HCl. Extraction with ethyl acetate gave a crude product which was purified by reverse phase HPLC eluting with an ammonium acetate buffer in aqueous acetonitrile to give 25 mg of compound 23.

Example 4

Additional Compounds Prepared.

The compounds shown in Table 1 have been prepared using procedures outlined in Schemes 1–10, or by modifications of these procedures known to those skilled in the art.

TABLE I (I)

| No. | $R^1$ | $R^2$ | $R^3$ | $R^4$ | $R^5$ | $R^6$ | $R^7$ | $R^8$ | $R^9$ | $R^{10}$ |
|---|---|---|---|---|---|---|---|---|---|---|
| 20 | H | *1 | H | H | H | $CO_2H$ | H | H | H | H |
| 21 | H | *2 | H | H | H | H | H | H | H | $CH_2CO_2H$ |
| 23 | H | $NHCH_3$ | H | H | H | $CO_2H$ | H | H | H | $CO_2H$ |
| 24 | H | H | H | $CO_2H$ | H | H | H | H | H | $CH_2CO_2H$ |
| 25 | H | H | H | H | H | $CO_2H$ | H | H | H | H |
| 26 | $OCH_3$ | $OCH_3$ | $OCH_3$ | H | H | $CO_2H$ | H | H | H | H |
| 27 | H | H | H | H | H | $CO_2CH_3$ | H | H | H | H |
| 28 | H | H | H | H | $CH_3$ | $CO_2H$ | H | H | H | $OCH_3$ |
| 29 | H | *2 | H | H | H | $CO_2CH_3$ | H | H | H | $OCH_3$ |
| 30 | H | *2 | H | H | H | $CO_2H$ | H | H | H | $OCH_3$ |
| 31 | H | *1 | H | H | H | $CO_2H$ | H | H | H | $OCH_3$ |
| 32 | H | *2 | H | H | H | $CO_2CH_3$ | H | F | H | H |
| 33 | H | *1 | H | H | H | $CO_2H$ | H | F | H | H |
| 34 | H | *2 | H | H | H | $CO_2CH_3$ | H | H | H | F |
| 35 | H | *1 | H | H | H | $CO_2H$ | H | H | H | F |
| 36 | H | *2 | H | H | H | $CO_2H$ | H | H | H | $SO_3H$ |
| 37 | H | *2 | H | H | H | $CO_2CH_3$ | H | H | F | H |
| 38 | H | H | H | H | H | H | $CO_2H$ | H | H | H |
| 39 | H | *2 | H | H | H | H | $CO_2CH_3$ | H | H | H |
| 40 | H | *4 | H | H | H | $CO_2CH_3$ | H | H | H | H |
| 41 | OH | H | OH | H | H | $CO_2H$ | H | H | H | H |
| 42 | H | H | $OCH_3$ | H | H | $CO_2H$ | H | H | H | H |
| 43 | H | *3 | H | H | H | $CO_2H$ | H | H | H | H |
| 44 | H | *2 | H | H | H | H | H | H | H | $CH_2CO_2CH_3$ |
| 45 | H | *2 | H | H | $CH_3$ | H | H | H | $CH_2CO_2H$ | H |
| 46 | H | *2 | H | H | H | H | H | H | $CH_2CO_2H$ | H |
| 47 | H | *2 | H | H | $CH_3$ | H | H | H | H | $CH_2CO_2H$ |
| 48 | H | *2 | H | H | $CH_3$ | H | H | H | H | $CH_2CO_2CH_3$ |
| 49 | H | *2 | H | H | $CH_3$ | H | H | H | $CO_2H$ | OtBu |
| 50 | H | *1 | H | H | $CH_3$ | H | H | H | $CO_2H$ | OtBu |
| 51 | H | *1 | H | H | $CH_3$ | H | H | H | $CO_2H$ | OH |
| 52 | H | $OCH_3$ | $OCH_3$ | H | H | $CO_2CH_3$ | H | H | H | H |
| 53 | H | $OCH_3$ | $OCH_3$ | H | H | $CO_2H$ | H | H | H | H |
| 54 | $OCH_3$ | H | $OCH_3$ | H | H | $CO_2H$ | H | H | H | H |
| 55 | H | H | $OCH_3$ | H | H | $CO_2CH_3$ | H | H | H | H |
| 56 | H | $OCH_2O$ | | H | H | H | H | H | H | $OCH_3$ |
| 57 | H | *1 | H | H | *5 | $CO_2H$ | H | H | H | $OCH_3$ |
| 58 | H | *1 | H | H | H | H | $CO_2H$ | H | H | H |
| 59 | *6 | H | *6 | H | H | $CO_2H$ | H | H | H | H |
| 60 | *7 | H | *7 | H | H | $CO_2H$ | H | H | H | H |
| 61 | *8 | H | *8 | H | H | $CO_2H$ | H | H | H | H |

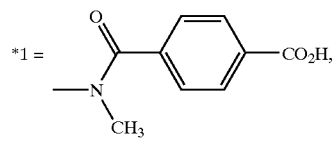

*1 =

TABLE I-continued

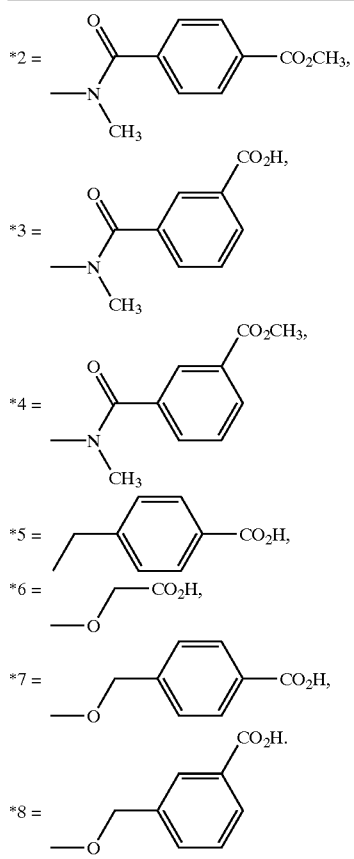

The IUPAC names of the compounds shown in Table 1, above, are listed below in Table 2. These names were generated using Chemistry 4D Draw™ from ChemInnovation Software, Inc.

TABLE 2

| No. | IUPAC Name |
| --- | --- |
| 20 | 5-((1E)-2-phenylvinyl)-2-({4-[(4-carboxyphenyl)-N-methylcarbonylamnino]phenyl}-N-methylcarbonylamino)benzoic acid |
| 21 | 4-((1E)-2-{4-[(4- {[4-(methoxycarbonyl)phenyl]-N-methylcarbonylamino}phenyl)-carbonylamino]phenyl}vinyl)benzoic acid |
| 23 | 5-[(1E)-2-(4-carboxyphenyl)vinyl]-2-{[4-(methylamino)phenyl]carbonylamino}-benzoic acid |
| 24 | 2-[N-(4-{(1E)-2-[4-(carboxymethyl)phenyl]vinyl}phenyl)carbamoyl]benzoic acid |
| 25 | 5-((1E)-2-phenylvinyl)-2-(N-methylphenylcarbonylamino)benzoic acid |
| 26 | 5-((1E)-2-phenylvinyl)-2-[(3,4,5-trimethoxyphenyl)carbonylamino]benzoic acid |
| 27 | methyl 5-((1E)-2-phenylvinyl)-2-[phenylcarbonylamino)benzoate |
| 28 | 5-[(1E)-2-(4-methoxyphenyl)vinyl]-2-(N-methylcarbonylamino)benzoic acid |
| 29 | methyl 4-{N-[4-(N-{4-[(1E)-2-(4-methoxyphenyl)vinyl]-2-(methoxycarbonyl)-phenyl}carbamoyl)phenyl]-N-methylcarbamoyl}benzoate |
| 30 | 5-[(1E)-2-(4-methoxyphenyl)vinyl]-2-[(4-{[4-(methoxycarbonyl)phenyl]-N-methyl-carbonylamino}phenyl)carbonylamino]benzoic acid |
| 31 | 5-[(1E)-2-(4-methoxyphenyl)vinyl]-2-({4-[(4-carboxyphenyl)-N-methylcarbonyl-amino]phenyl}carbonylamino)benzoic acid |
| 32 | methyl 4- {N-[4-(N- {4-[(1E)-2-(2-fluorophenyl)vinyl]-2-(methoxycarbonyl)phenyl}-carbamoyl)phenyl]-N-methylcarbamoyl}benzoate |
| 33 | 5-[(1E)-2-(2-fluorophenyl)vinyl]-2-({4-[(4-carboxyphenyl)-N-methylcarbonyl-amino]phenyl}carbonylamino)benzoic acid |
| 34 | methyl 4-{N-[4-(N-{4-[(1E)-2-(4-fluorophenyl)vinyl]-2-(methoxycarbonyl)phenyl}-carbamoyl)phenyl]-N-methylcarbamoyl}benzoate |
| 35 | 5-[(1E)-2-(4-fluorophenyl)vinyl]-2-({4-[(4-carboxyphenyl)-N-methylcarbonyl-amino]phenyl}carbonylamino)benzoic acid |
| 36 | 4-((1E)-2-{3-(methoxycarbonyl)-4-[(4- {[4-(methoxycarbonyl)phenyl]-N-methyl-carbonylamino}phenyl)carbonylamino]phenyl}vinyl)benzenesulfonic acid |

TABLE 2-continued

| No. | IUPAC Name |
|---|---|
| 37 | methyl 4-{N-[4-(N-{4-[(1E)-2-(3-fluorophenyl)vinyl]-2-(methoxycarbonyl)phenyl}-carbamoyl)phenyl]-N-methylcarbamoyl}benzoate |
| 38 | 2-((1E)-2-phenylvinyl)-5-(phenylcarbonylamino)benzoic acid |
| 39 | 2-((1E)-2-phenylvinyl)-5-[(4-{[4-(methoxycarbonyl)phenyl]-N-methylcarbonyl-amino}phenyl)carbonylamino]benzoic acid |
| 40 | methyl 4-[N-(4-{N-[4-((1E)-2-phenylvinyl)-2-(methoxycarbonyl)phenyl]-carbamoyl}phenyl)-N-methylcarbamoyl]benzoate |
| 41 | 5-((1E)-2-phenylvinyl)-2-[(3,5-dihydroxyphenyl)carbonylamino]benzoic acid |
| 42 | 5-((1E)-2-phenylvinyl)-2-[(3-methoxyphenyl)carbonylamino]benzoic acid |
| 43 | 5-((1E)-2-phenylvinyl)-2-({4-[(4-carboxyphenyl)-N-methylcarbonylamino]-phenyl}carbonylamino)benzoic acid |
| 44 | methyl 4-(N-{4-[N-(4-{(1E)-2-[4-(methoxycarbonyl)phenyl]vinyl}phenyl)-carbamoyl]phenyl}-N-methylcarbamoyl)benzoate |
| 45 | 2-[3-((1E)-2-{4-[(4-{[4-(methoxycarbonyl)phenyl]-N-methylcarbonylamino}-phenyl)-N-methylcarbonylamino]phenyl}vinyl)phenyl]acetic acid |
| 46 | 2-[3-((1E)-2- {4-[(4- {[4-(methoxycarbonyl)phenyl]-N-methylcarbonylamino}-phenyl)carbonylamino]phenyl}vinyl)phenyl]acetic acid |
| 47 | 4-((1E)-2-{4-[(4-{[4-(methoxycarbonyl)phenyl]-N-methylcarbonylamino}phenyl)-N-methylcarbonylamino]phenyl}vinyl)benzoic acid |
| 48 | methyl 4-(N-{4-[-(4-{(1E)-2-[4-(methoxycarbonyl)phenyl]vinyl}phenyl)-N-methylcarbamoyl]phenyl}-N-methylcarbamoyl)benzoate |
| 49 | 5-((1E)-2-{4-[(4-{[4-(methoxycarbonyl)phenyl]-N-methylcarbonylamino}phenyl)-N-methylcarbonylamino]phenyl}vinyl)-2-(tert-butoxy)benzoic acid |
| 50 | 5-{(1E)-2-[4-({4-[(4-carboxyphenyl)-N-methylcarbonylamino]phenyl}-N-methyl-carbonylamino)phenyl]vinyl}-2-(tert-butoxy)benzoic acid |
| 51 | 5-{(1E)-2-[4-({4-[(4-carboxyphenyl)-N-methylcarbonylamino]phenyl}-N-methyl-carbonylamino)phenyl]vinyl}-2-hydroxybenzoic acid |
| 52 | methyl 5-((1E)-2-phenylvinyl)-2-[(3,4-dimethoxyphenyl)carbonylamino]benzoate |
| 53 | 5-((1E)-2-phenylvinyl)-2-[(3,4-dimethoxyphenyl)carbonylamino]benzoic acid |
| 54 | 5-((1E)-2-phenylvinyl)-2-[(3,5-dimethoxyphenyl)carbonylamino]benzoic acid |
| 55 | 2-{5-((1E)-2-phenylvinyl)-2-[(3-methoxyphenyl)carbonylamino]phenyl}acetic acid |
| 56 | N-{4-[(1E)-2-(4-methoxyphenyl)vinyl]phenyl}-2H-benzo[d]1,3-dioxolen-5-yl-carboxamide |
| 57 | 5-[(1E)-2-(4-methoxyphenyl)vinyl]-2-(N-[(4-carboxyphenyl)methyl]{4-[(4-carboxy-phenyl)-N-methylcarbonylamino]phenyl}carbonylamino)benzoic acid |
| 58 | 2-((1E)-2-phenylvinyl)-5-({4-[(4-carboxyphenyl)-N-methylcarbonylamino]phenyl}-carbonylamino)benzoic acid |
| 59 | 5-((1E)-2-phenylvinyl)-2-{[3,5-bis(carboxymethoxy)phenyl]carbonylamino}benzoic acid |
| 60 | 5-((1E)-2-phenylvinyl)-2-({3,5-bis[(4-carboxyphenyl)methoxy]phenyl}carbonyl-amino)benzoic acid |
| 61 | 5-((1E)-2-phenylvinyl)-2-({3,5-bis[(3-carboxyphenyl)methoxy]phenyl}carbonyl-amino)benzoic acid |

Example 5

$^{32}$P-CKD Autophosphorylation Assay.

The complete β-kinase domain of the human insulin receptor (CKD) was expressed in, and purified from, baculovirus. CKD (4.0 μg/ml), in a solution of 29 mM HEPES (pH 7.6), 0.05% Triton X-100, 10 mM MgCl$_2$, 2 mM MnCl$_2$ (50 μl final volume), is combined with 50 μM ATP, and 5 μCi $^{32}$P-ATP (3000 Ci/mmol). A test compound, or the vehicle (dimethyl sulfoxide (DMSO) was added to a final DMSO concentration of 1%. The mixture was incubated for 10 minutes at room temperature. The reaction was terminated by the addition of 10 μl of 200 mM EDTA. A 30 μl volume was removed, mixed with 5 μl of 6×Laemmeli sodium dodecyl sulfate (SDS) treatment buffer, and heated to 94° C. for 5 minutes. A 20 μl aliquot was then run on an SDS-PAGE gel. The radioactivity incorporated into the CKD band is quantified by phosphorimaging of the gel, or scintillation counting of the excised bands. The potency of a compound (at 10 μM concentration) for increasing phosphorylation was expressed as % of the vehicle level. The results for this assay are shown in Table 3.

TABLE 3

| Compound No. | Activity (% vs. control) |
|---|---|
| 20 | 112 |
| 21 | 92 |
| 23 | 112 |
| 24 | 126 |
| 25 | 59 |
| 26 | 107 |
| 27 | 73 |
| 28 | 75 |
| 29 | 61 |
| 30 | 93 |
| 31 | 121 |
| 32 | 81 |
| 33 | 78 |
| 34 | 88 |
| 35 | 177 |
| 36 | 171 |
| 37 | 93 |
| 38 | 105 |
| 39 | 64 |
| 41 | 80 |
| 42 | 123 |
| 44 | 97 |
| 46 | 91 |
| 49 | 81 |
| 50 | 105 |

TABLE 3-continued

| Compound No. | Activity (% vs. control) |
|---|---|
| 52 | 54 |
| 53 | 105 |
| 55 | 117 |
| 56 | 51 |
| 57 | 107 |
| 59 | 94 |
| 60 | 80 |

Example 6

Glucose Transport Activity.

3T3 L1 fibroblasts (ATCC) were grown in Dulbecco's modified Eagle's medium (DMEM) with 10% fetal bovine serum (FBS). The cells were plated at a density of $3 \times 10^4$ cells/well in 24-well plates. Two days after confluence was reached, the cells were treated for 3 days with 0.5 mM isobutylmethylxanthine (IBMX), 1 µM dexamethasone, and 1.7 µM insulin. The cells were then transferred to DMEM with 1.7 µM insulin for 2 more days. The cells were maintained in DMEM with 10% FBS for an additional 4 days. Finally, the cells were serum-starved overnight in 0.1% bovine serum albumin (BSA) in DMEM. The following day, the medium was replaced with 150 mM NaCl, 1.7 mM KCl, 0.9 mM $CaCl_2$, $K_2HPO_4$ (pH 7.4), to which was added either the experimental compound or its vehicle (DMSO). Insulin or its vehicle (0.01% BSA) was diluted in the assay buffer (containing test compound or vehicle, respectively) to a final concentration of 5.6 nM. After incubation for 30 min at 37° C., 5 µCi/ml $^{14}C$-2-deoxy-D-glucose was added, and the incubation was continued for an additional 30 min at 37° C. The cells were then washed 3 times with ice-cold PBS/20 mM glucose and lysed in 250 µl of lysis buffer (50 mM HEPES pH 7.6, 1% Triton X-100) for 30 min at room temperature. Radioactivity in the lysate was quantified by scintillation counting.

Once $^{14}C$-2-deoxy-D-glucose is transported into the cell, it is not released. Glucose transport is, therefore, proportional to the amount of radioactivity in the lysate. The compounds were tested at concentrations from 1 µM to 56 µM. The concentration of compound necessary to produce an increase in glucose transport that is 50% of the response of 100 nM insulin (using 5.6 nM insulin as the lower bound) was calculated as the $EC_{50}$ (effective concentration). The results are shown in Table 4.

TABLE 4

| Compound No. | $EC_{50}$ (µM) |
|---|---|
| 20 | 109 |
| 21 | 23 |
| 23 | 98 |
| 24 | 414 |

Example 7

Oral Pharmaceutical Composition Preparation—
Solid Dosage Formulation.

A pharmaceutical composition for oral administration may be prepared by combining the following:

| | % w/w |
|---|---|
| Compound of this invention | 10% |
| Magnesium stearate | 0.5% |
| Starch | 2.0% |
| Hydroxypropylmethylcellulose | 1.0% |
| Microcrystalline cellulose | 86.5% |

The mixture may be compressed to tablets or filled into hard gelatin capsules.

The tablets may be coated by applying a suspension of film former (e.g., hydroxypropylmethylcellulose), pigment (e.g., titanium dioxide), and plasticizer (e.g., diethyl phthalate) and drying the film via evaporation of the solvent. The film coat can comprise 2% to 6% of the tablet weight, preferably about 3%, Example 8

Oral Pharmaceutical Composition Preparation—
Capsule.

A pharmaceutical composition of a compound of the invention suitable for oral administration may also be prepared by combining the following:

| | % w/w |
|---|---|
| Compound of this invention | 20% |
| Polyethylene glycol 400 | 80% |

The medicinal compound is dispersed in the liquid carrier with a thickening agent added, if required. The formulation is then enclosed in a soft gelatin capsule by suitable technology.

Example 9

Pharmaceutical Composition for Parental Administration.

A pharmaceutical composition for parenteral administration may be prepared by combining the following:

| | % w/w |
|---|---|
| Compound of this invention | 1.0% |
| Saline | 99.0% |

The solution is sterilized and sealed in sterile containers.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What we claim is:
1. A compound of formula I:

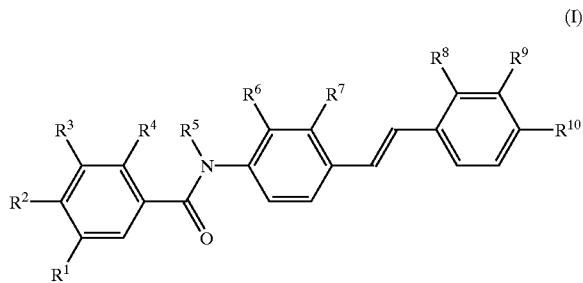

where
$R^1$, $R^2$, $_3$, and $R^4$ are, independently, hydrogen, hydroxyl, or optionally substituted lower alkyloxy;
$R^5$ is hydrogen, lower alkyl, substituted lower alkyl, or aryl;
$R^6$ is —C(O)$OR^{13}$, where $R^{13}$ is hydrogen or lower alkyl;
$R^7$ is hydrogen, lower alkyl or —C(O)$OR^{13}$, where $R^{13}$ has the above meaning;
$R^8$ and $R^9$ are, independently, hydrogen, lower alkyl, substituted lower alkyl, halo, hydroxyl, lower alkoxy, carboxyl, —$NR^{11}R^{12}$, or —C(O)$NR^{11}R^{12}$, where $R^{11}$ and $R^{12}$ are, independently, hydrogen, lower alkyl, substituted lower alkyl aryl, substituted aryl, aryl (lower)alkyl, substituted aryl(lower)alkyl, heteroaryl (lower)alkyl substituted heteroaryl(lower)alkyl, heterocyclyl, substituted heterocyclyl, heteroaryl or substituted heteroaryl,
$R^{10}$ is hydrogen, lower alkyl, substituted lower alkyl, halo, hydroxy, lower alkoxy, —C(O)$OR^{13}$ where $R^{13}$ has the above meaning, —$SO_3H$, or —C(O)$NR^{11}R^{12}$, where $R^{11}$ and $R^{12}$ have the above meanings;
or a pharmaceutically acceptable salt thereof;
as a single stereoisomer or mixture of stereoisomers.

2. The compound of claim 1 that is selected from the group consisting of:
5-((1E)-2-phenylvinyl)-2-(N-methylphenylcarbonylamino)benzoic acid, 5-((1E)-2-phenylvinyl)-2-[(3,4,5-trimethoxyphenyl)carbonylamino]benzoic acid, methyl 5-((1E)-2-phenylvinyl)-2-(phenylcarbonylamino)benzoate, 5-[(1E)-2-(4-methoxyphenyl)vinyl]-2-(N-methylphenylcarbonylamino)benzoic acid, 5-((1E)-2-phenylvinyl)-2-[(3,5-dihydroxyphenyl)carbonylamino] benzoic acid, 5-((1E)-2-phenylvinyl)-2-[(3-methoxyphenyl)carbonylamino]benzoic acid, methyl 5-((1E)-2-phenylvinyl)-2-[(3,4-dimethoxyphenyl)carbonylamino]benzoate, 5-((1E)-2-phenylvinyl)-2-[(3,4-dimethoxyphenyl)carbonylamino]benzoic acid, 5-((1E)-2-phenylvinyl)-2-[(3,5-dimethoxyphenyl)carbonylamino]benzoic acid, methyl 5-((1E)-2-phenylvinyl)-2-[(3-methoxyphenyl)carbonylamino]benzoate, and 5-((1E)-2-phenylvinyl)-2-{[3,5-bis(carboxymethoxy)phenyl]carbonylamino}benzoic acid,
and the pharmaceutically acceptable salts thereof.

3. A method of enhancing glucose uptake comprising administration to a mammal of a therapeutically effective amount of a compound according to claim 1.

4. The method of claim 3, where the mammal suffers from non-insulin dependent diabetes mellitus, hyperglycemia, or another disease involving imbalance of glucose levels.

5. A pharmaceutical composition comprising:
(a) a compound according to claim 1 as an active ingredient; and
(b) a pharmaceutically acceptable carrier.

6. The pharmaceutical composition of claim 5 for treating a mammalian disease state selected from the group consisting of hyperglycemia, type I diabetes, and type II diabetes.

7. A method of stimulating the kinase activity of the insulin receptor, comprising contacting the insulin receptor, or the kinase portion thereof, with a compound according to claim 1 in an amount sufficient to stimulate the kinase activity of the insulin receptor.

8. A method of activating the insulin receptor, comprising contacting the insulin receptor, or the kinase portion thereof, with a compound according to claim 1 in an amount sufficient to activate the insulin receptor.

9. The method of claim 8, where the insulin receptor is on the surface of a cell in a mammal, and where the compound may be administered in the form of a pharmaceutical composition.

10. A method of stimulating the uptake of glucose into cells displaying the insulin receptor, comprising contacting the cells in vitro or in vivo with a compound according to claim 1 in an amount sufficient to stimulate the uptake of glucose into the cells.

11. The method of claim 10, where the insulin receptor is on the surface of a cell in a mammal, and where the compound may be administered in the form of a pharmaceutical composition.

12. The method of any one of claims 7 to 11, further comprising contacting the insulin receptor with insulin.

13. A method of obtaining and/or developing a compound that has the function of stimulating the kinase activity of the insulin receptor, activating the insulin receptor, and/or stimulating the uptake of glucose, the method comprising using a compound of claim 1 as a model.

14. A method for validating, optimizing, or standardizing a bioassay, comprising using of a compound of claim 1 as a standard.

15. A radiolabelled compound of claim 1.

16. A method for the treatment of a disease state selected from hyperglycemia, type I diabetes, type II diabetes, and another disease involving imbalance of glucose levels in a mammal, comprising administering to the mammal a therapeutically effective amount of a compound of claim 1.

17. A method for the treatment of a disease state selected from hyperglycemia, type I diabetes, type II diabetes, or another disease involving imbalance of glucose levels in a mammal, comprising co-administering to the mammal a compound of claim 1 and insulin.

18. The method of claim 17 where the amount of insulin administered would be sub-therapeutic for the disease state if administered alone.

19. A method for the treatment of a disease state selected from hyperglycemia, type I diabetes, type II diabetes, or another disease involving imbalance of glucose levels in a mammal, comprising co-administering to the mammal a compound of claim 1 and a non-insulin drug.

20. The method of claim 19 where the amount of non-insulin drug administered would be sub-therapeutic for the disease state if administered alone.

21. A method for the treatment of type II diabetes, comprising co-administering to the mammal a compound of claim 1, insulin, and a non-insulin antidiabetic agent.

22. The method of claim 21 where the amount of insulin would be sub-therapeutic if administered alone.

* * * * *